(12) United States Patent
Nakamura et al.

(10) Patent No.: US 7,951,541 B2
(45) Date of Patent: May 31, 2011

(54) ASSAY KIT FOR USE IN METHOD OF DETECTING A TARGET NUCLEIC ACID

(75) Inventors: Naoko Nakamura, Kawasaki (JP); Keiko Ito, Kawasaki (JP)

(73) Assignee: Kabushiki Kaisha Toshiba, Tokyo (JP)

(*) Notice: Subject to any disclaimer, the term of this patent is extended or adjusted under 35 U.S.C. 154(b) by 0 days.

(21) Appl. No.: 12/851,675

(22) Filed: Aug. 6, 2010

(65) Prior Publication Data
US 2011/0021379 A1 Jan. 27, 2011

Related U.S. Application Data

(62) Division of application No. 11/624,814, filed on Jan. 19, 2007, now Pat. No. 7,803,544.

(30) Foreign Application Priority Data

Jan. 20, 2006 (JP) ................. 2006-012889

(51) Int. Cl.
*C12Q 1/68* (2006.01)
*C12P 19/34* (2006.01)
(52) U.S. Cl. .......................... 435/6; 435/91.2
(58) Field of Classification Search ............ 435/6, 91.2
See application file for complete search history.

(56) References Cited

U.S. PATENT DOCUMENTS
7,488,581 B2  2/2009  Nakamura et al.

FOREIGN PATENT DOCUMENTS

| EP | 0 971 039 A2 | 1/2000 |
|---|---|---|
| EP | 1 327 679 A1 | 7/2003 |
| EP | 1 564 301 A1 | 8/2005 |
| JP | 5-199898 | 8/1983 |
| JP | 62-282599 | 12/1987 |
| JP | 6-70799 | 3/1994 |
| JP | 2002-272475 | 9/2002 |
| JP | 2002-345499 | 12/2002 |
| JP | 2005-143492 | 6/2005 |
| WO | WO 00/28082 | 5/2000 |
| WO | WO 02/24902 | 3/2002 |

OTHER PUBLICATIONS

Saiki, et al., Science, 1985, vol. 230, pp. 1350-1354.

*Primary Examiner* — Kenneth R. Horlick
(74) *Attorney, Agent, or Firm* — Oblon, Spivak, McClelland, Maier & Neustadt, L.L.P.

(57) ABSTRACT

Kits for use in a method of detecting an amplification product by hybridizing it with a probe, the amplification product is amplified from a target nucleic acid with the primers, including placing F3, F2 and F1 regions in this order from a 5' terminal side and B3$c$, B2$c$ and B1$c$ regions in this order from a 3' terminal side, and additionally an FP region in the region from the F2 to F1 regions and/or a BPc region in the region from the B2$c$ to B1$c$ regions in the target nucleic acid, determining the respective regions in such a manner that the FP and F2 regions and/or the BPc and B2$c$ regions have an unoverlapping region of at least 10 bases or more and overlapping regions of 10 bases or less, and designing the primers according to the regions.

21 Claims, 18 Drawing Sheets

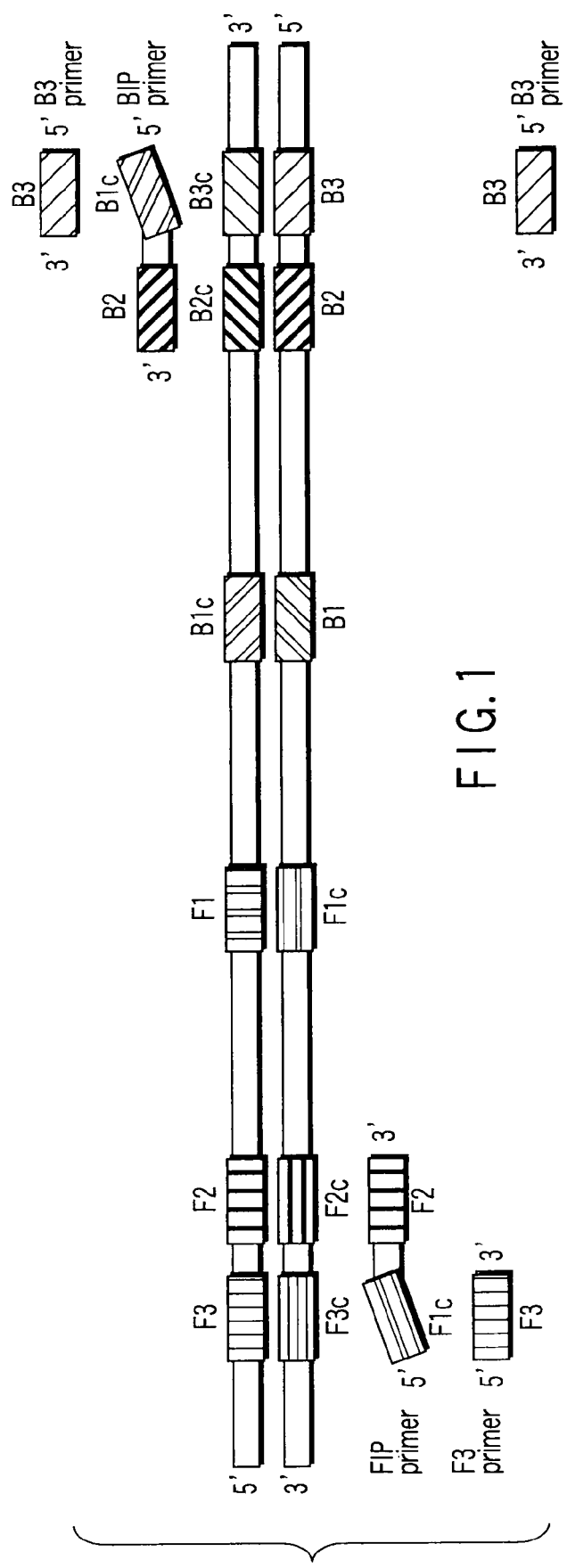
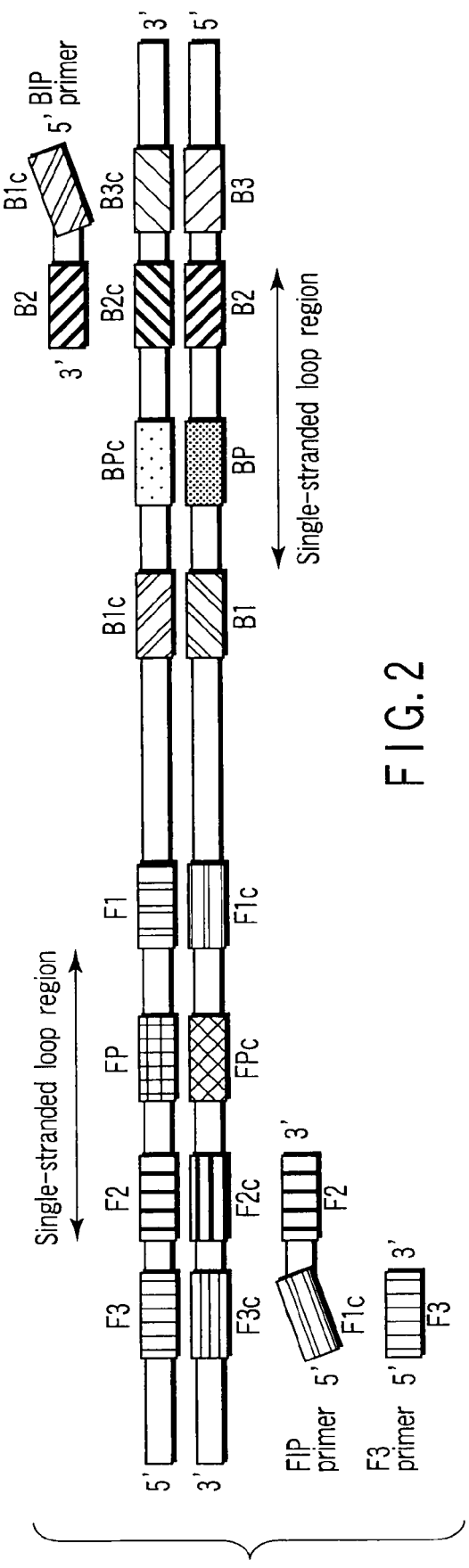
FIG. 1
FIG. 2

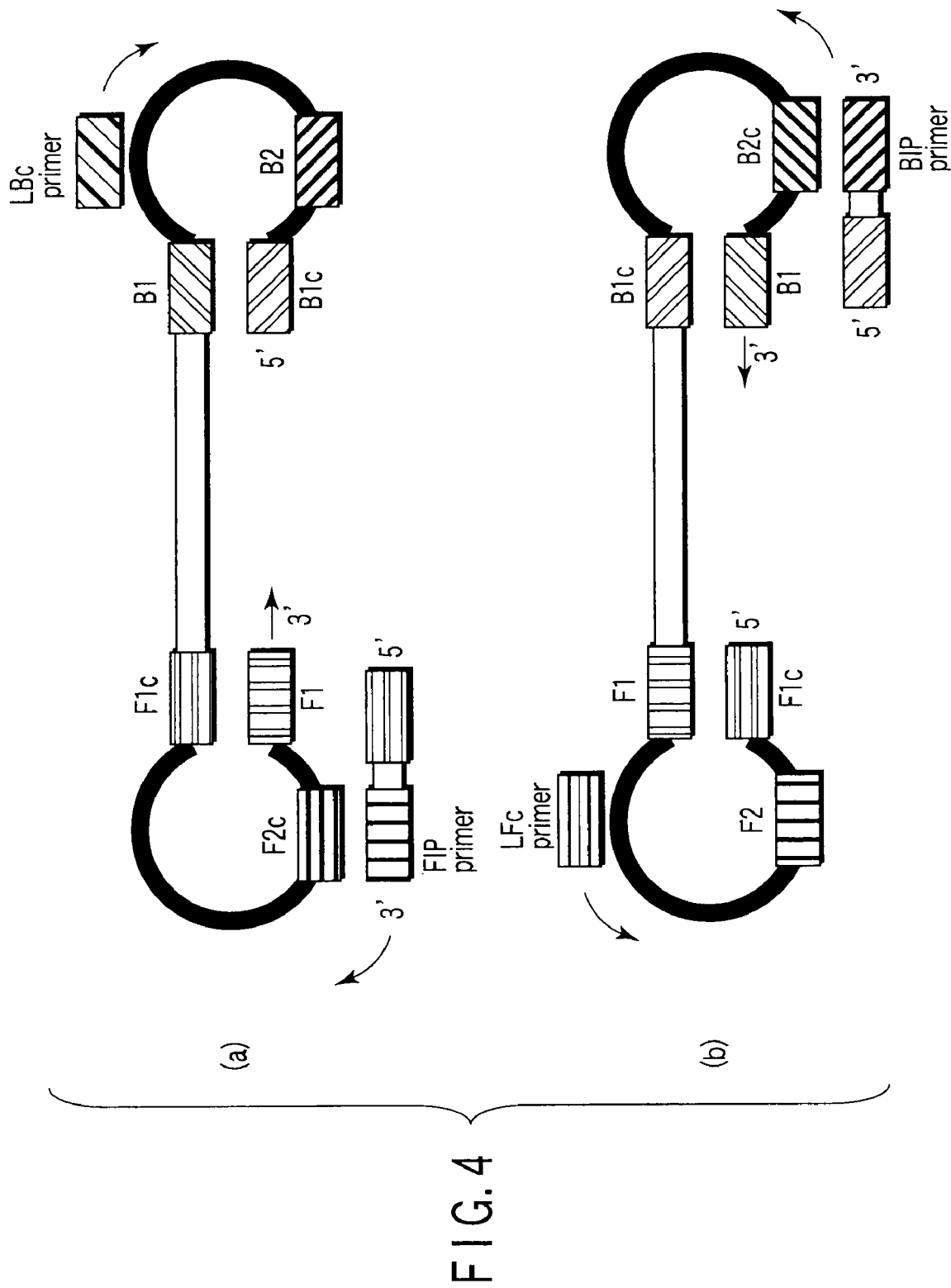
F I G. 4

FIG. 8

(a) Inhibition factor I

| Detection sequence | Probe nucleotide sequence | Inner primer | | Loop primer |
|---|---|---|---|---|
| FP plus chain | FPc minus chain | F1c minus chain | F2 plus chain | LFc minus chain |
| FPc minus chain | FP plus chain | F1c minus chain | F2 plus chain | LFc minus chain |
| BP minus chain | BPc plus chain | B1c plus chain | B2 minus chain | LBc plus chain |
| BPc plus chain | BP minus chain | B1c plus chain | B2 minus chain | LBc plus chain |

(b) Inhibition factor II

| Detection sequence | Probe nucleotide sequence | Inner primer | | Loop primer |
|---|---|---|---|---|
| FP plus chain | FPc minus chain | F1c minus chain | F2 plus chain | LFc minus chain |
| FPc minus chain | FP plus chain | F1c minus chain | F2 plus chain | LFc minus chain |
| BP minus chain | BPc plus chain | B1c plus chain | B2 minus chain | LBc plus chain |
| BPc plus chain | BP minus chain | B1c plus chain | B2 minus chain | LBc plus chain |

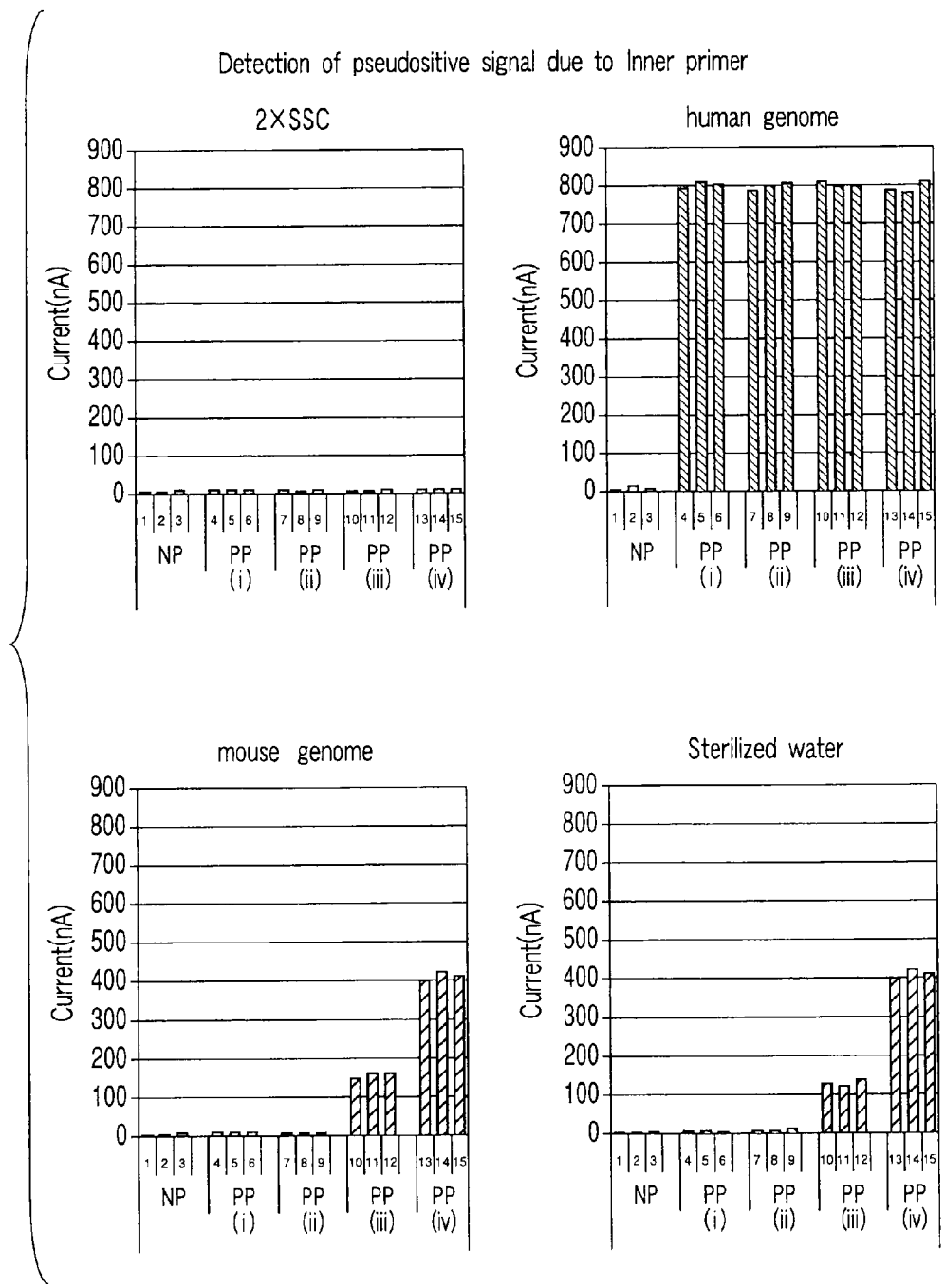
F I G. 12

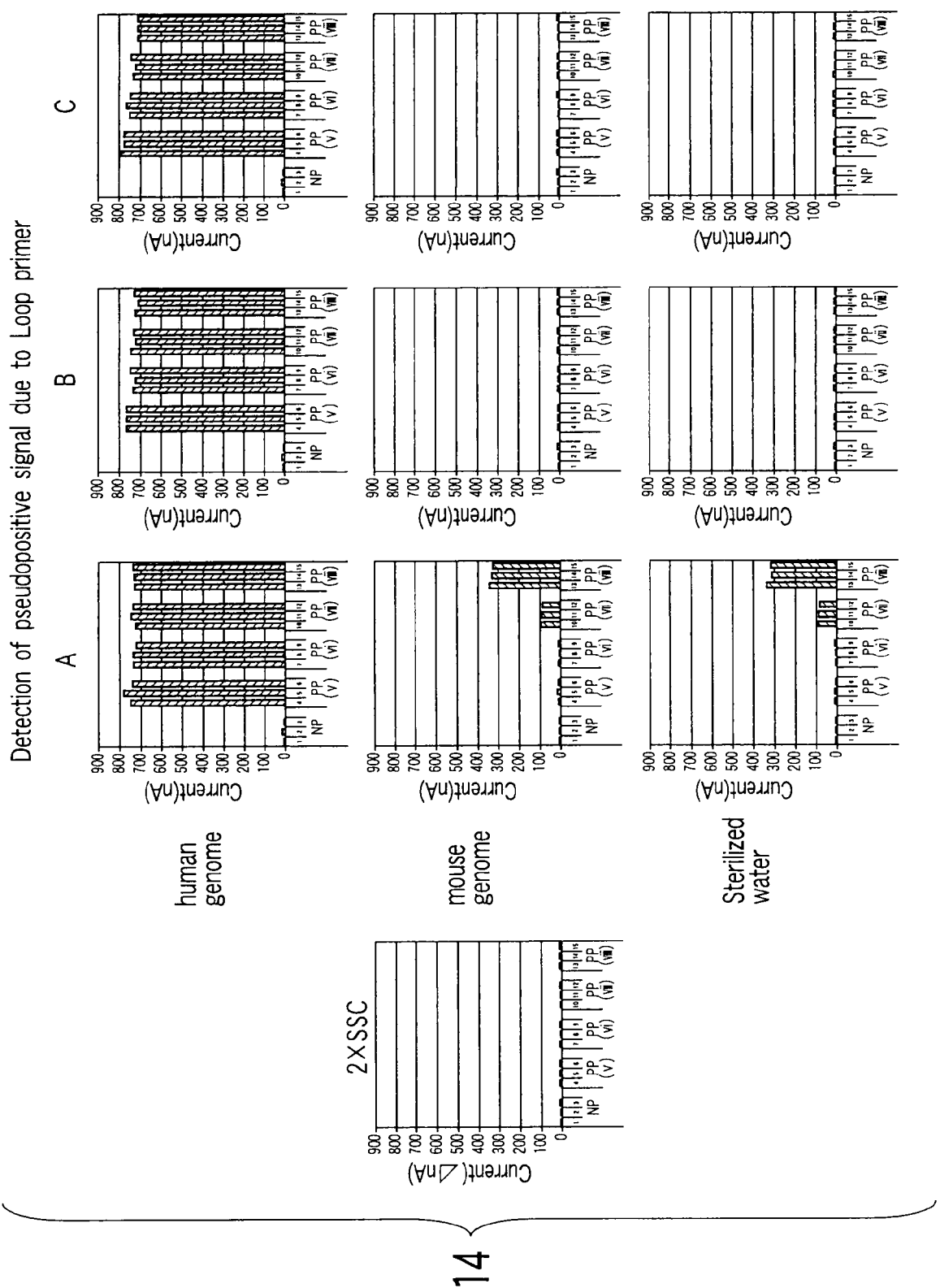
F I G. 14

| | A | B | C |
|---|---|---|---|
| Added primer | F3-primer, B3-primer, FIP-primer, BIP-primer, LFc-primer, and LBc-primer | F3-primer, B3-primer, FIP-primer, BIP-primer, and LBc-primer | F3-primer, B3-primer, FIP-primer, and BIP-primer |
| LAMP amplification efficiency | ○ Amplification saturated within 60 minutes | ○ Amplification saturated within 60 minutes | X Amplification saturated not within 60 or 90 minutes, but within 120 minutes |
| Current detection result | X Pseudopositive by hybridization between unreacted loop primer LFc and probe nucleic acid | ○ No pseudopositive signal | ○ No pseudopositive signal |

F I G. 15

| | A | B | C |
|---|---|---|---|
| Added primer | F3-primer, B3-primer, FIP-primer, BIP-primer, LFc-primer, and LBc-primer | F3-primer, B3-primer, FIP-primer, BIP-primer, and LBc-primer | F3-primer, B3-primer, FIP-primer, and BIP-primer |
| LAMP amplification efficiency | ○ Amplification saturated within 60 minutes | ○ Amplification saturated within 60 minutes | X Amplification saturated not within 60 or 90 minutes, but within 120 minutes |
| Current detection result | X Inhibition of hybridization reaction between probe and target nucleic acid by unreacted loop primer LFc | No hybridization inhibition | — |

F I G. 17

Design of loop primer and detection sequence containing single-nucleotide polymorphism site on NAT2 sequence

```
gtgggcttcatcctcacctatagaaaattcaattataaagacaatacagat
    F3 →                                    F2
ctggtcgagtttaaaactctcactgaggaagaggttgaagaagtgctgaaa
    ← →                  ←
       LFc                              F1c
aatatttaagatttccttggggagaaatctcgtgcccaa|acctggtgat
Detection sequences (iv) (v)      B1c →         LBc
gg/aatcccttactattt|agaataaggacaaaataaaccttgtgtatgt
    857SNP →                    ← B2
atcacccaactcactaattatcaacttatgtgctatcagatatcctcta
    ← B3
```

FIG. 18

| | D | E | D+E |
|---|---|---|---|
| Template | 857G/G home | 857A/A home | 857G/G home+857A/A home |
| Added primer | F3-primer, B3-primer, FIP-primer, and BIP-primer | F3-primer, B3-primer, FIP-primer, and BIP-primer | F3-primer, B3-primer, FIP-primer, and BIP-primer |
| LAMP amplification efficiency | ○ Amplification saturated within 60 minutes | ○ Amplification saturated within 60 minutes | ○ Amplification saturated within 60 minutes |
| Current detection result | ○ Higher current in case G | ○ Higher current in case G | ○ Higher current in both cases G and A |

| | F | G | H | I |
|---|---|---|---|---|
| Template | 857G/A hetero | | | |
| Added primer | F3-primer, B3-primer, FIP-primer, BIP-primer, LFc-primer, and LBcA-primer | F3-primer, B3-primer, FIP-primer, BIP-primer, and LBcG-primer | F3-primer, B3-primer, FIP-primer, BIP-primer, and LFc-primer | F3-primer, B3-primer, FIP-primer, and BIP-primer |
| LAMP amplification efficiency | ○ Amplification saturated within 30 minutes | ○ Amplification saturated within 30 minutes | ○ Amplification saturated within 30 minutes | ○ Amplification saturated within 60 minutes |
| Current detection result | × Higher current in case A | × Higher current in case G | ○ Higher current in both cases A and G | ○ Higher current in both cases A and G |

FIG. 20

ASSAY KIT FOR USE IN METHOD OF DETECTING A TARGET NUCLEIC ACID

CROSS-REFERENCE TO RELATED APPLICATIONS

This application is a divisional of U.S. application Ser. No. 11/624,814, filed Jan. 19, 2007 (now U.S. Pat. No. 7,803,544). It is based upon and claims the benefit of priority from prior Japanese Patent Application No. 2006-012889, filed Jan. 20, 2006, the entire contents of which are incorporated herein by reference.

BACKGROUND OF THE INVENTION

1. Field of the Invention

The present invention relates to a method of designing primers for amplification of a target nucleic acid and a method of detecting the target nucleic acid by using the primer, and an assay kit for the method.

2. Description of the Related Art

For detection a nucleic acid chain having a particular nucleotide sequence, the nucleic acid is amplified by using a nucleotide primer complementary thereto. The amplification product is generally identified by electrophoresis or hybridization with a probe complementary to the sequence to be detected in the amplification product. The hybridization with a probe has the advantage that it is possible to reconfirm the specificity of amplification product.

A polymerase chain reaction (PCR) method is generally known as the gene amplification method (see, e.g., Science, 230, pp. 1350-54, 1985). However, the method has problems such as demand for complicated temperature control unit and low specificity to templates with mutation only of several bases.

Recently, a loop-mediated isothermal amplification (LAMP) method has been developed as a gene amplification method demanding no such complicated temperature control (see JP No. 3313358). The LAMP method is a method of amplifying a particular gene region under an isothermal condition at 60 to 65° C. The LAMP method use primers including an inner primer pair, an outer primer pair, and optionally loop primer pairs (see WO No. 02/024902), a strand-displacing polymerase, and a substrate nucleotide. The LAMP method gives a greater amount of final product than the PCR method. It also has advantages such as simple operation, high speed, and low cost. Accordingly, the LAMP method is expected to be used in wider fields.

The PCR products are present in the double-stranded chain structure. For this reason, when the PCR product is detected with a probe nucleic acid, its complementary chain of the PCR product inhibit as a competitor to the probe, so hybridization efficiency has decreased. To solve the problem, developed was a method of preventing self hybridization of the nucleic acid to be detected by binding a nucleic acid chain to a target nucleic acid chain in the region excluding the sequence region complementary to the probe thereof (see, e.g., JP-A 6-70799 [KOKAI]). However, even the method does not give sufficient sensitivity. Alternatively developed was a method of decomposing or separating the complementary chain in the PCR product. However, the method also had problems such as high cost due to use of enzyme, magnetic beads and the like and complicated operation.

On the other hand, the LAMP product has a single-stranded loop region therein. Therefore, it is possible to design the region to bind with a probe. In this way, it is possible to hybridize a probe with the product efficiently without a step of converting the product into single strands. Disclosed were various methods of detecting a LAMP amplification product by using a single-stranded loop region. For example, JP-A 2002-272475 (KOKAI) discloses a method of labeling a probe hybridizing with the single-stranded loop region with fluorescent dye and measuring its fluorescent polarization. Alternatively, JP-A 2002-345499 (KOKAI) discloses a method of immobilizing the 5' terminal of a primer hybridizing with a single-stranded loop region on an immobilization carrier and monitoring its coagulation reaction. Yet alternatively, JP-A 2005-143492 (KOKAI) discloses a method of immobilizing a probe hybridizing with a single-stranded loop region on a solid phase and detecting the hybridization between the probe and the LAMP amplification product based on the fluorescent or electrochemical principle.

However, for the detection methods using a single-stranded region, there is no principle of design regions of primers and detection regions closed each other. Thus, there exists a need for an improved detection method for detecting the LAMP-amplified product efficiently.

BRIEF SUMMARY OF THE INVENTION

An object of the present invention is to provide a method of designing LAMP primers for accurate detection of LAMP amplification product.

According to one aspect of the present invention, there is provided a method of designing primers for use in a method of detecting an amplification product by hybridizing it with a probe, the amplification product is amplified from a target nucleic acid with the primers, on the presupposition that:

the target nucleic acid comprise F3, F2 and F1 regions in this order from a 5' terminal side, B3c, B2c and B1c regions in this order from a 3' terminal side, as well as an FP region in the region from the F2 to F1 regions and/or a BPc region in the region from the B2c to B1c regions;

the probe represents a probe nucleic acid comprising a nucleotide sequence complementary to a sequence selected from the group consisting of the sequence in the FP and BPc region and the sequences complementary thereto; and the primers contain an FIP primer comprising the sequence identical to that of the F2 region at the 3' terminal side and a sequence complementary to that of the F1 region at the 5' terminal side; an F3 primer comprising the sequence identical to that of the F3 region; a BIP primer comprising a sequence complementary to that of the B2c region at the 3' terminal side and the sequence identical to that of the B1c region at the 5' terminal side; and a B3 primer comprising a sequence complementary to that of the B3c region:

the method comprising setting the respective regions in such a manner that the FP and F2 regions and/or the BPc and B2c regions have an unoverlapping region of at least 10 bases or more and overlapping regions of 10 bases or less, and designing the primers according to the regions.

According to another aspect of the present invention, there is provided a method of designing primers for use in a method of detecting a single-nucleotide mutation by amplifying a target nucleic acid having the single-nucleotide mutation with primers and hybridizing the amplification product with a probe, on the presupposition that:

the target nucleic acid comprise F3, F2 and F1 regions in this order from a 5' terminal side, B3c, B2c and B1c regions in this order from a 3' terminal side, as well as an FP region having the single-nucleotide mutation in the region from the F2 to F1 regions and/or a BPc region having the single-nucleotide mutation in the region from the B2c to B1c regions;

the probe represents a probe nucleic acid comprising a nucleotide sequence complementary to a sequence selected from the group consisting of the sequence in the FP and BPc region, and the sequences complementary thereto; and, the primers contain an FIP primer comprising the sequence identical to that of the F2 region at the 3' terminal side and a sequence complementary to that of the F1 region at the 5' terminal side; an F3 primer comprising the sequence identical to that of the F3 region; a BIP primer comprising a sequence complementary to that of the B2c region at the 3' terminal side and the sequence identical to that of the B1c region at the 5' terminal side; and a B3 primer comprising a sequence complementary to that of the B3c region:

the method comprising setting the F2 region not to overlap the single-nucleotide mutation in the FP region and/or the B2c region not to overlap the single-nucleotide mutation in the BPc region, and designing the primers according to the regions.

BRIEF DESCRIPTION OF THE SEVERAL VIEWS OF THE DRAWING

FIG. 1 is a chart showing the locations of respective regions on a target nucleic acid;

FIG. 2 is a chart showing the locations of detection regions on a target nucleic acid;

FIG. 4 is a chart showing LAMP-amplification intermediate products and primer-annealing sites;

FIG. 8 is a table showing the relationship between respective sequences when the inner and loop primers are factors inhibiting the probe nucleic acid;

FIG. 12 is a chart showing the detection result of the pseudopositive signals caused by inner primers;

FIG. 14 is a chart showing the detection result of the pseudopositive signals caused by loop primers;

FIG. 15 is a chart showing the relationship between the kind of primer added in Example 2 and the amplification efficiency and detection result;

FIG. 17 is a chart showing the relationship between the kind of primer added in Example 3 and the amplification efficiency and detection result;

FIG. 18 is a chart showing an embodiment of respective regions placed on a NAT2 gene (SEQ ID NO: 57);

FIG. 20 is a chart showing the relationship between the kind of primer added in Example 4 and the amplification efficiency and detection result.

DETAILED DESCRIPTION OF THE INVENTION

Figure 3:
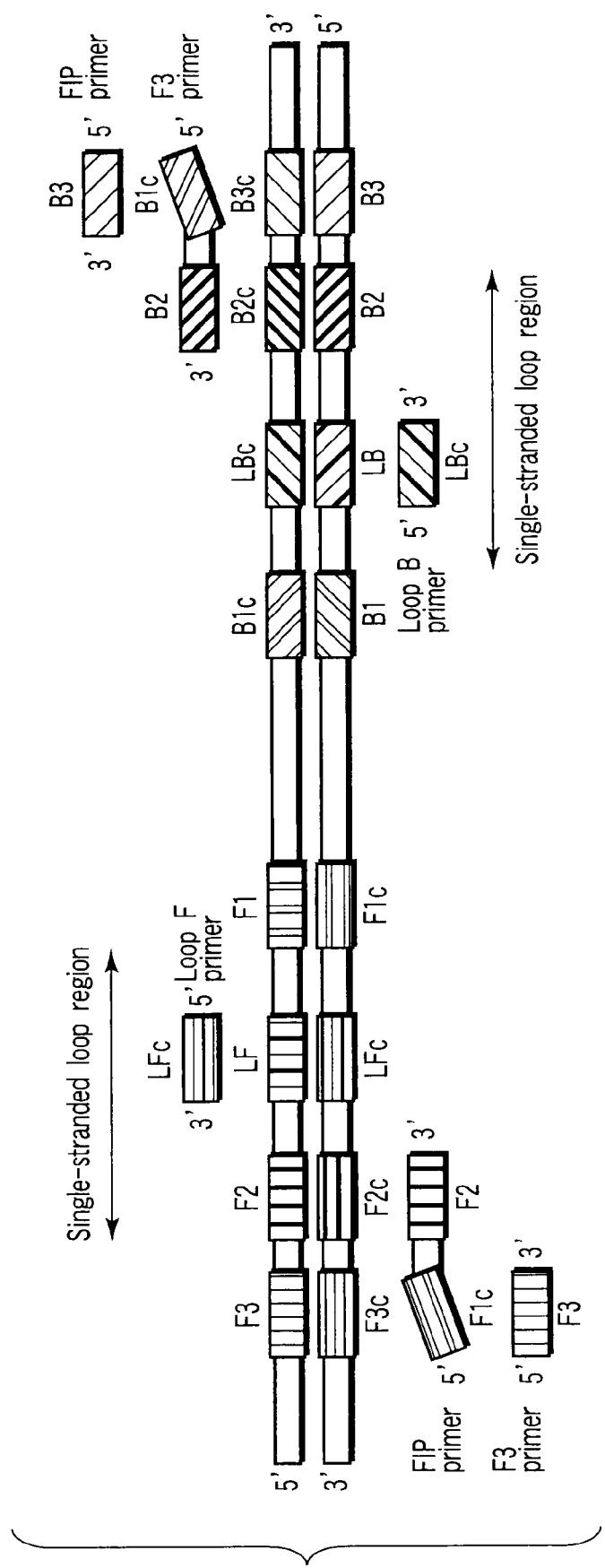
FIG. 3 is a chart showing the location of a loop primer region on a target nucleic acid.

The inventors have found that the primer used for amplification of LAMP product is a cause of inhibition of and deterioration in reaction efficiency of the hybridization reaction, and completed the present invention. It is possible to easily obtain a LAMP amplification product with higher hybridization efficiency, by using a primer designed according to the present invention. It is thus possible to detect a particular target nucleic acid easily at high accuracy.

Hereinafter, aspects of the present invention will be described in detail. In the present specification, the nucleic acid to be detected is called a target nucleic acid, and the nucleotide sequence thereof is called target sequence. The solution possibly containing the target nucleic acid used in the detection method according to the present invention will be called a sample solution.

In the present invention, in which the products amplified by LAMP method are detected after hybridization with a probe nucleic acid, the sequence in the amplification product used in hybridization with the probe nucleic acid will be referred to as detection sequence. Accordingly, the probe nucleic acid has a sequence complementary to the detection sequence.

The LAMP method is a method of amplifying a target nucleic acid present in a sample by using primers and a chain-substituting DNA polymerase. There are various methods of detecting the amplification product, but the present invention relates to a detection method by using a probe nucleic acid as described above. Hereinafter, the LAMP method will be described briefly.

As shown in FIG. 1, in the LAMP method, F3, F2 and F1 regions are placed in this order from the 5' terminal side of a target nucleic acid, and B3c, B2c and B1c regions are placed in this order from the 3' terminal side thereof. In the method according to the present invention of detecting an amplification product by hybridizing it with a probe nucleic acid, an FP region is placed additionally in the region from the F2 to F1 regions and a BPc region in the region from the B2c to B1c regions, as shown in FIG. 2. The FP and BPc regions and the regions of their complementary chains are the detection regions with which the probe nucleic acid is hybridized and of which the nucleotide sequences are detected. The sequence for use in detection by hybridization with a probe nucleic acid may be just one of the sequences in the FP and BPc regions and sequences complementary thereto, or two or more of them may be used at the same time. Thus, the sequence of the probe nucleic acid is prepared to have a sequence complementary to the detection sequence among the sequences above.

The regions having complementary sequence to those of the F3, F2, and F1 regions will be called F3c, F2c, and F1c regions, respectively. The regions having complementary sequence to those of the B3c, B2c, and B1c regions will be called B3, B2, and B1 regions, respectively. Similarly, the regions having complementary sequence to those of the FP and BPc regions will be called FPc and BP regions. In the present specification, the chains having the F3 region or the like will be called plus chains, while the chains having the F3c region or the like will be called minus chains, for convenience.

A primer used for amplification of nucleic acids in the LAMP method includes four kinds of basic primers: (1) an FIP primer having the sequence identical to that of the F2 region in the 3' terminal side and a sequence complementary to that of the F1 region at the 5' terminal side; (2) an F3 primer having the sequence identical to that of the F3 region; (3) a BIP primer having a sequence complementary to that of the B2c region at the 3' terminal side and the sequence identical to that of the B1c region at the 5' terminal side; and (4) a B3 primer having a sequence complementary to that of the B3c region. Generally, the FIP and BIP primers are called inner primers, while the F3 and B3 primers are called outer primers.

The amplification period in the LAMP method can be shortened by optionally using a primer called a loop primer. In such a case, as shown in FIG. 3, an LF region is placed in the region from the F2 to F1 regions and an LBc region is placed in the region from the B2c to B1c regions of a target nucleic acid. These regions will be referred to as loop primer regions. In addition to the four kinds of primers above, a loop primer LFc having a sequence complementary to that of the LF region and a loop primer LBc having the sequence identical to that of the LBc region are used. See WO 2002/024902 for details. These loop primers LFc and LBc may be used alone or in combination.

FIG. 4 is a schematic chart showing intermediate amplification products by the LAMP method. In the LAMP method, dumbbell-shaped intermediate products are first produced from the target nucleic acid, as shown in the figure, and become the initial points in the amplification cycle. The methods of generating the initial point structure and subsequent amplifying are known in the art, and see JP No. 3313358 for details. As shown in FIG. 4, the intermediate products, which have complementary sequences at both terminals, form loops by self-annealing.

As shown in FIG. 4, the FIP and BIP primers become synthetic initial points by annealing respectively on the intermediate products, and thus, the synthetic reaction proceeds from the 3' terminal side. The intermediate products having the loop structure function as templates for the FIP and BIP primers continuously, allowing progress of the nucleic acid synthesis. As shown in the figure, the loop primer anneals on a loop different from the loops annealed by the FIP and BIP primers, becoming an additional synthetic initial point to accelerate amplification.

Because it is advantageous to use the single-stranded loop region in the reaction of hybridizing a LAMP amplification product with a probe nucleic acid, the detection region is placed in the loop region.

Figure 5:
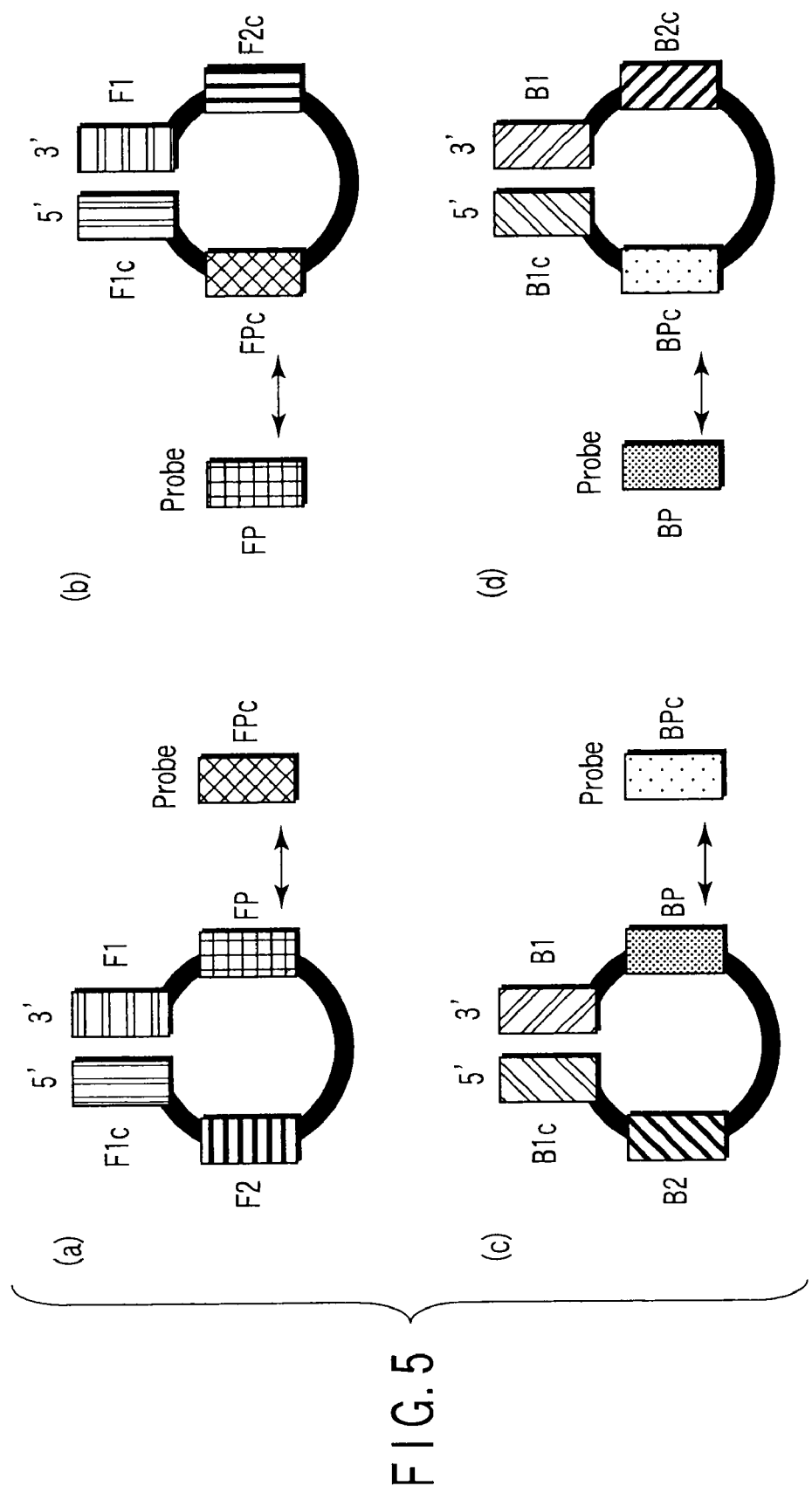
FIG. 5 is a schematic chart showing four kinds of single-stranded loop regions formed in a LAMP product.

FIG. 5 is a schematic chart showing four kinds of single-stranded loop regions formed from the LAMP amplification product. The loop regions have respectively the FP or BPc regions or the regions complementary thereto as detection regions, and the figure also shows probe nucleic acids hybridizing with the detection sequences. As shown in FIG. 5, the four kinds of probe nucleic acids may be used for detection of the amplification products, but just one or two kinds of the probe nucleic acids may be used suitably.

In a first aspect of the present invention, the FP and F2 regions are designed to have an unoverlapping region of at least 10 bases or more and overlapping regions of 10 bases or less. Similarly, the BPc and B2c regions are designed to have an unoverlapping region of at least 10 bases or more and overlapping regions of 10 bases or less. Preferably, the overlapping region has a length of zero to 10 bases, more preferably zero to 5 bases. As these regions are designed to satisfy the conditions above, other regions are also designed suitably, and the primers are designed properly according to the regions.

Primer design according to the conditions, with respective regions satisfying the condition above, is important for improving the hybridization efficiency between the amplification products and the probe nucleic acids. The reason will be described below in detail with reference to FIG. 6.

Figure 6:
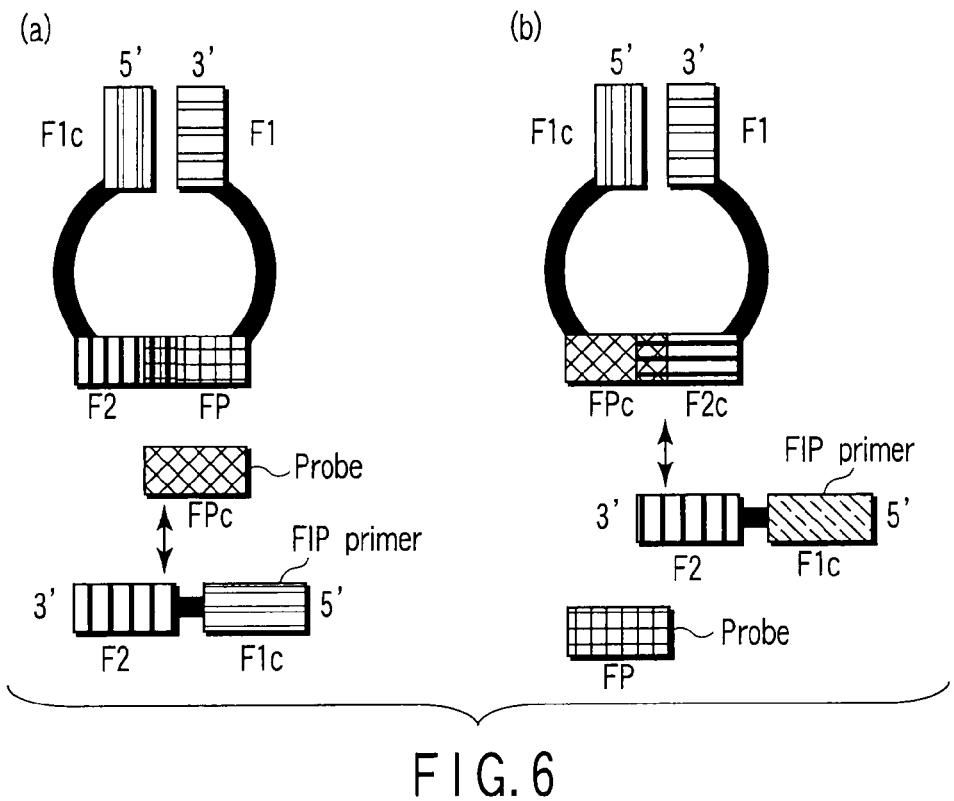
FIG. 6 is a schematic chart showing an F2 region and an FP region overlapping each other.

FIG. 6 is a schematic chart showing the FP region and the F2 region largely overlapping each other. FIG. 6A shows a case where the FP region is located in the loop structure, i.e., when it is a plus chain. The probe nucleic acid at this time has a sequence complementary to that of the FP region (i.e., sequence of the FPc region). There is still the unreacted FIP primer in the reaction solution, which has the same sequence as that of the F2 region. As a result, as shown in FIG. 6A, the unreacted FIP primer and the probe nucleic acid hybridize with each other with the sequence of the overlapping FP and F2 regions. Accordingly, the unreacted FIP primer, which functions as a competitive substance to the amplification product, leads to deterioration of the hybridization efficiency between the amplification products and the probe nucleic acids. In addition, the unreacted primer may give rise to a pseudopositive signal by hybridization thereof with the probe nucleic acid, even when the target nucleic acid is not amplified.

FIG. 6B shows a case where the FPc region is located in the loop structure, i.e., when it is a minus chain. As shown in FIG. 2, the nucleic acid chain has the F2c region complementary to the F2 region. Because the F2c region is complementary to the F2 region in FIP primer, the unreacted FIP primer forms a double-stranded chain by annealing on the F2c region, leading to inhibition of the hybridization between the amplification product and the probe nucleic acid. The influence is fatal, particularly during real-time detection or high-sensitivity high-accuracy or detection of amplification products.

In summary, the hybridization inhibition factors described above may be divided into the following two groups: (I) reactions between an unreacted primer and a probe nucleic acid, and (II) reactions between an unreacted primer and an amplification product. These inhibition factors seem to cause problems such as deterioration of hybridization reaction efficiency and detection accuracy.

Hereinafter, a second aspect of the present invention where a loop primer is used will be described. In such a case, the FP and LF regions are designed to have an unoverlapping region of at least 10 bases or more and overlapping regions of 10 bases or less. Similarly, the BPc and LBc regions are designed to have an unoverlapping region of at least 10 bases or more and overlapping regions of 10 bases or less. As these regions are designed to satisfy the conditions above, other regions are also designed suitably, and the primers are designed properly according to the regions designed.

Also in the second aspect, significant overlapping between the FP region and the loop primer region may lead to deterioration of hybridization efficiency, as with the first aspect. For example as shown in FIG. 7A, in the case of a plus chain, the unreacted loop primer LFc forms a double-stranded chain by annealing on the LF region in the amplification product and inhibits hybridization with the probe nucleic acid FPc. Thus, the reaction is influenced by the inhibition factor (II). Also in the case of a minus chain, the unreacted loop primer LFc hybridizes with the probe nucleic acid FP, inhibiting hybridization between the amplification product and the probe nucleic acid, as shown in FIG. 7B. The unreacted loop primer may hybridize with the probe nucleic acid even when the target nucleic acid is not amplified, giving rise to a pseudopositive signal. Thus, the reaction is influenced by the inhibition factor (I).

Figure 7:
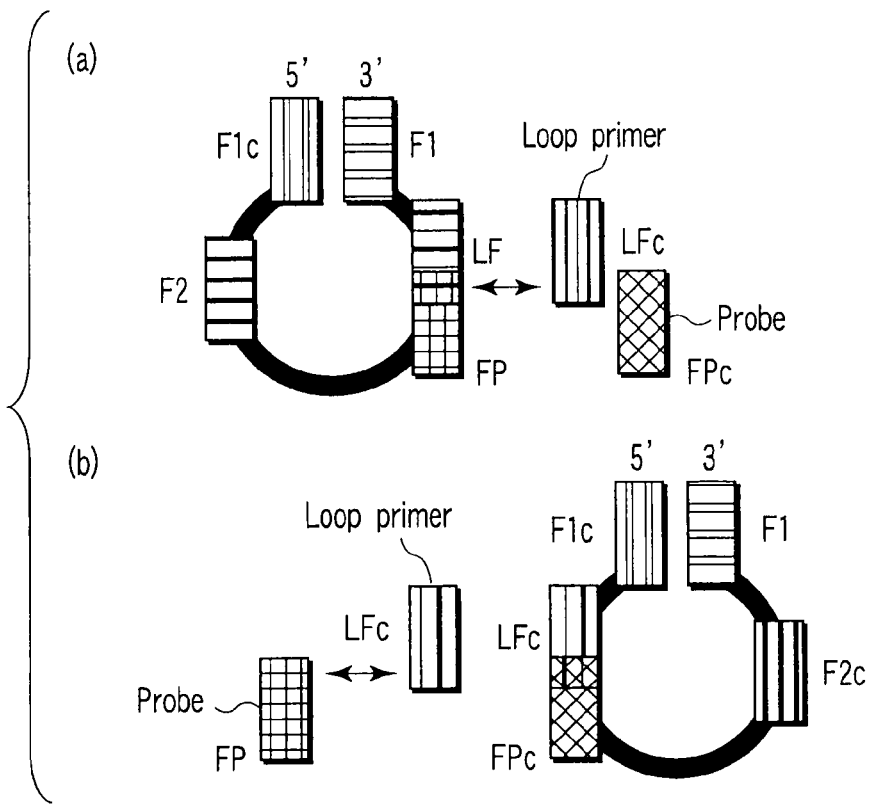
FIG. 7 is a schematic chart showing an LF region and an FP region overlapping each other.

In FIG. 7, the F2, FP, and LF regions are placed in this order, but may be placed in the order of F2, LF, and FP regions.

FIG. 8 shows a list of the inhibition factors. Relationships when the unreacted primer gives a pseudopositive signal with respect to the probe nucleic acid (inhibition factor I) are shown as shaded in FIG. 8A. The inhibition factor (I) is generated, when the sequences of the target nucleotides in the amplification product, and the sequences in the inner primers (FIP and BIP primers) or the sequences of loop primers (LFc and LBc primers) are the same chain (i.e., they are both plus chains or minus chains). In other words, the sequence of the probe nucleic acid and the sequence of the inner or loop primer are reverse to each other.

FIG. 8B shows relationships where the unreacted primer competes with the probe nucleic acid (inhibition factor II) as they are shaded. The inhibition factor (II) is generated, when the sequences of the target nucleic acids in the amplification product and the sequences of the inner or loop primers are reverse to each other. In other words, the sequence of the probe nucleic acid and the sequence of the inner or loop primer are same chain.

As described above, when any two of the FP, F2, and LF regions or the BP, B2, and LBc regions are overlapping each other, the overlapping region affects or inhibits hybridization and reduces its efficiency, if the overlapping region is excessively large. Noticing the problem above and after intensive studies, the inventors have found that it was possible to eliminate such influences or reduce them into an allowable range by shortening the overlapping region to 10 bases or less, as shown in the Examples below.

The two regions having an overlapping region of 10 bases or less may become vulnerable to the influences, if the base number of the other unoverlapping regions is too small, and thus, the unoverlapping regions preferably have a sequence of 10 bases or more. The length of the unoverlapping region is not particularly limited, as long as it is incorporated in the single-stranded loop-structured region, and may be determined arbitrarily according to the sequence of the target nucleic acid and the relationship between the sequence of each primer and the detection sequence.

Figure 9:
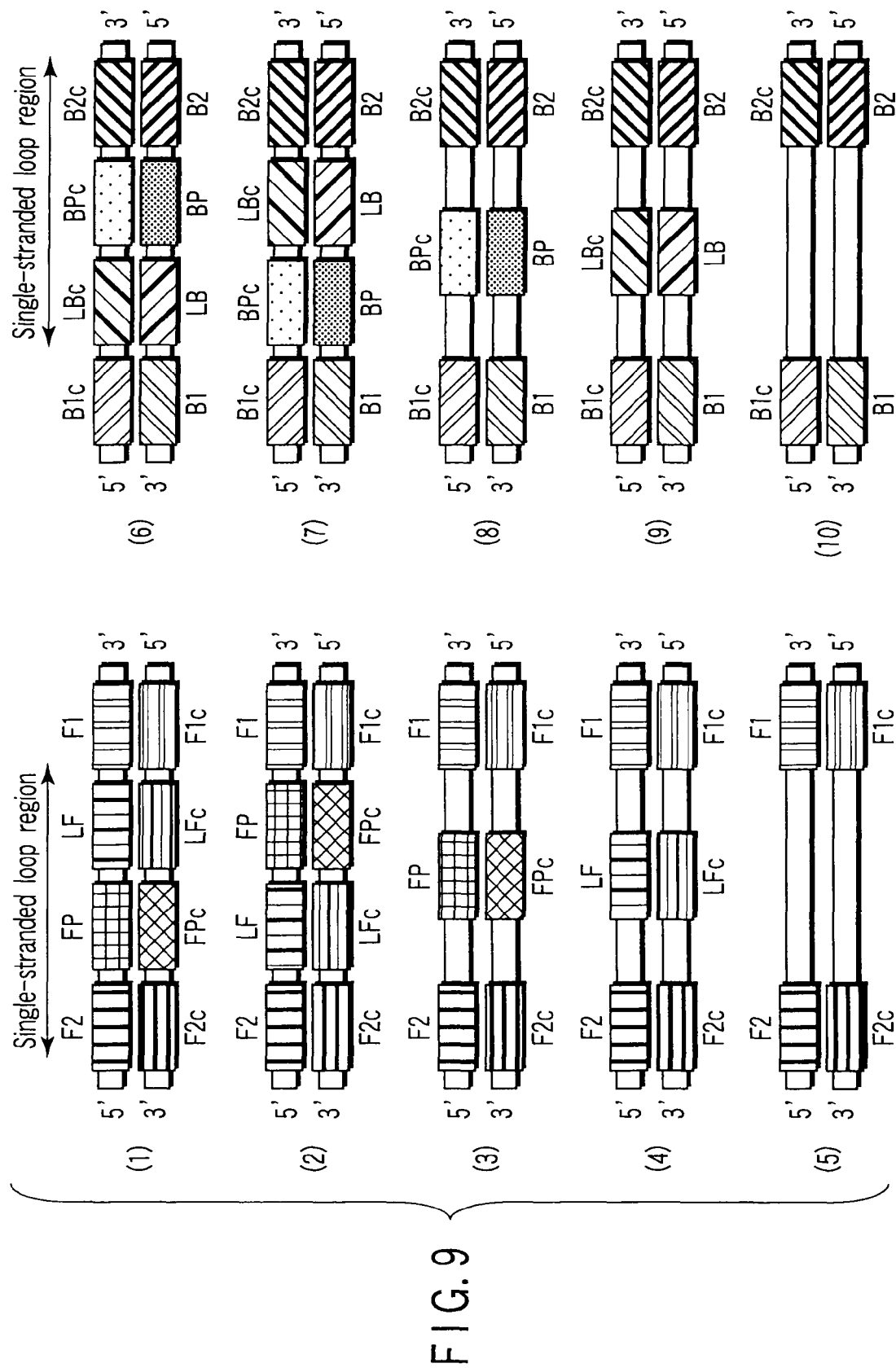
FIG. 9 is a chart showing the design patterns of respective regions placed on a target nucleic acid.

FIG. 9 shows design patterns of detection sequence regions (FP, FPc, BP, and BPc), inner primer sequence regions (F1c+F2 and B1c+B2), and loop primer sequence regions (LFc and LBc) of each of the plus and minus chains of the target nucleic acid chain. FIGS. 9(1) and 9(2) show cases where both the detection sequence and the loop primer are located in the F region side. In FIG. 9(1), the FP region and the F2 or LF region are designed to have an unoverlapping region of at least 10 bases or more and overlapping regions of 10 bases or less.

The reason for making the overlapping region between the FP region and the F2 or LF region 10 bases or less is already described. For example, when the detection sequence is a plus chain (FP), the F2 region may cause the inhibition factor I, while the LFc region may cause the inhibition factor II. When the detection sequence is a minus chain (FPc), the LFc region may cause the inhibition factor I, while the F2 region may cause the inhibition factor II.

The overlapping region between the LF and F1 regions is 20 bases or less, more preferably 10 bases or less in length. It is because the loop primer LFc should anneal on the double-stranded chain in the F1-F1c region, leading to decrease in amplification efficiency, when the base number in the overlapping region between the LF and F1 regions is increased.

In the case of FIG. 9(2), the FP and LF regions are designed to have an unoverlapping region of at least 10 bases or more and overlapping regions of 10 bases or less. The reason for making the overlapping region between the FP and LF regions 10 bases or less is already described. For example, when the detection sequence is a plus chain (FP), the LFc region causes the inhibition factor II. When the detection sequence is a minus chain (FPc), the LFc causes the inhibition factor I.

The number of bases in the duplicated region of the FP and F1 region is preferably less than 15, more preferably zero. When the overlapping region between the FP and F1 regions is 15 bases or more in length, the F1c region causes the inhibition factor I, when the minus chain (FPc) is detected. It is because the probe nucleic acid should hybridize with the double-stranded F1-F1c region, leading to decrease in hybridization efficiency.

The base number of the overlapping region between the F2 and LF regions is preferably 20 or less, more preferably 10 or less. When the F2 and LF regions overlap each other over a length of 20 bases, the sequences of the FIP primer containing the F2 sequence and the loop primer LFc are complementary to each other in the overlapping region, resulting in interaction between the primers. As a result, the primers become less reactive with the amplification product on which it anneals, leading to decrease in amplification efficiency.

FIG. 9(3) shows a case where there is no loop primer in the F region side. For the same reason as in FIGS. 9(1) and 9(2), the FP and F2 regions are designed to have an unoverlapping region of at least 10 bases or more and overlapping regions of 10 bases or less. The FP and F1 regions are also designed to have an overlapping region of less than 15 bases, more preferably zero base in length.

FIG. 9(4) shows a case where there is no detection sequence placed in the F region side. The case 9(4) may be combined with the cases 9(6) to 9(8) where the detection sequences are placed in the B region. For the same reason as in FIGS. 9(1) and 9(2), the F2, LF, and F1 regions are designed to have an unoverlapping region of 20 bases or less and more preferably 10 bases or less.

FIG. 9(5) shows a case where there is no loop primer or detection sequence placed in the F region side. The case 9(5) may be combined with the cases 9(6) to 9(8) where the detection sequences are placed in the B region. The F2 and F1 regions are preferably separated from each other by 5 bases or more for improvement of self-annealing efficiency.

FIGS. 9(6) to 9(10) showing the B region are similar to the cases showing the F region side. The cases 9(9) and 9(10) where there is no detection sequence, may be combined with the cases 9(1) to 9(3) where detection sequences are placed in the F region side.

As shown in FIGS. 9(1), 9(2), 9(6) and 9(7), presence of a detection sequence region and a loop primer sequence region in the same loop occasionally results in deterioration of self-annealing efficiency and also in amplification efficiency, by elongation of the chain in the single-stranded loop region, depending on the sequence of the target nucleic acid. In such a case, it is effective to place a loop primer not in the loop region containing a detection sequence, but in another loop region.

In a third aspect, the present invention provides a method of designing a primer used in the method of detecting single-nucleotide mutation (single-nucleotide polymorphism) by the LAMP method. The amplification method and the detection method by using a probe nucleic acid by the LAMP method are the same as those in the first and second aspects, but the site of single-nucleotide mutation in the target nucleic acid is designed to be included in the region of FP or BP, for detection of the single-nucleotide mutation. Thus, F3, F2 and F1 regions are placed in this order from the 5' terminal side of a target nucleic acid, B3c, B2c and B1c regions are placed in this order from the 3' terminal side, and additionally, an FP region containing single-nucleotide mutation is placed in the region from the F2 to F1 regions above. Alternatively, the BPc region containing single-nucleotide mutation may be located in the region from the B2c to B1c regions.

The primer used in the present aspect is the same as that used in the first aspect. In the third aspect, the F2 region is designed not to overlap the single-nucleotide mutation site in the FP region.

Alternatively, the B2c region is designed not to overlap the single-nucleotide mutation site in the BPc region. As these regions are designed to satisfy the conditions above, other regions are also designed suitably, and the primers are designed properly according to the regions designed.

For detection of single-nucleotide mutation, the amplification product may be hybridized after it is amplified completely with a probe nucleic acid. Hybridization with the probe nucleic acid then is determined by the base at the single-nucleotide mutation site in the amplification product. In this method, reaction condition should be restricted owing to detect single-nucleotide mutation. Therefore, even if one should forget addition of a genome and an amplification reaction does not occur but a primer exists so much in solution, a probe and a primer does not hybridized each other. So they are not determined incorrectly. The restriction in primer design is thus alleviated, whether the unreacted primers remains among the amplification product, because only the difference in relative intensity of the signal associated with single-nucleotide mutation is to be differentiated. However, design of an inner or loop primer at the single-nucleotide mutation site or the site of its complementary chain results in preferential amplification of the genome with the genotype contained in the inner or loop primer, prohibiting production of the amplification product of the genotype inherent to the target nucleic acid.

It is thus important not to place an inner or loop primer sequence region at a position at the single-nucleotide mutation (single-nucleotide polymorphism) site in the target nucleic acid. The regions are determined according to the setting above and the primer is designed.

In a fourth aspect, the present invention provides a method of designing a primer used in the method of detecting single-nucleotide mutation by using a loop primer, as in the second aspect.

Thus, the LF region is placed in the region from the F2 to F1 regions, and the LBc region is placed in the region from the B2c to B1c regions. In addition to the primers above, the loop primer LFc consisting of the sequence complementary those of the LF region and the loop primer LBc consisting of the sequence identical to the LBc region are used in combination. In the fourth aspect of the present invention, the LFc region is placed at a position not overlapping the single-nucleotide mutation site in the FP region. Alternatively, the LBc region is placed at a position not overlapping the single-nucleotide mutation site in the BPc region. As these regions are designed to satisfy the conditions above, other regions are also designed suitably, and the primers are designed properly according to the regions designed.

Figure 10:
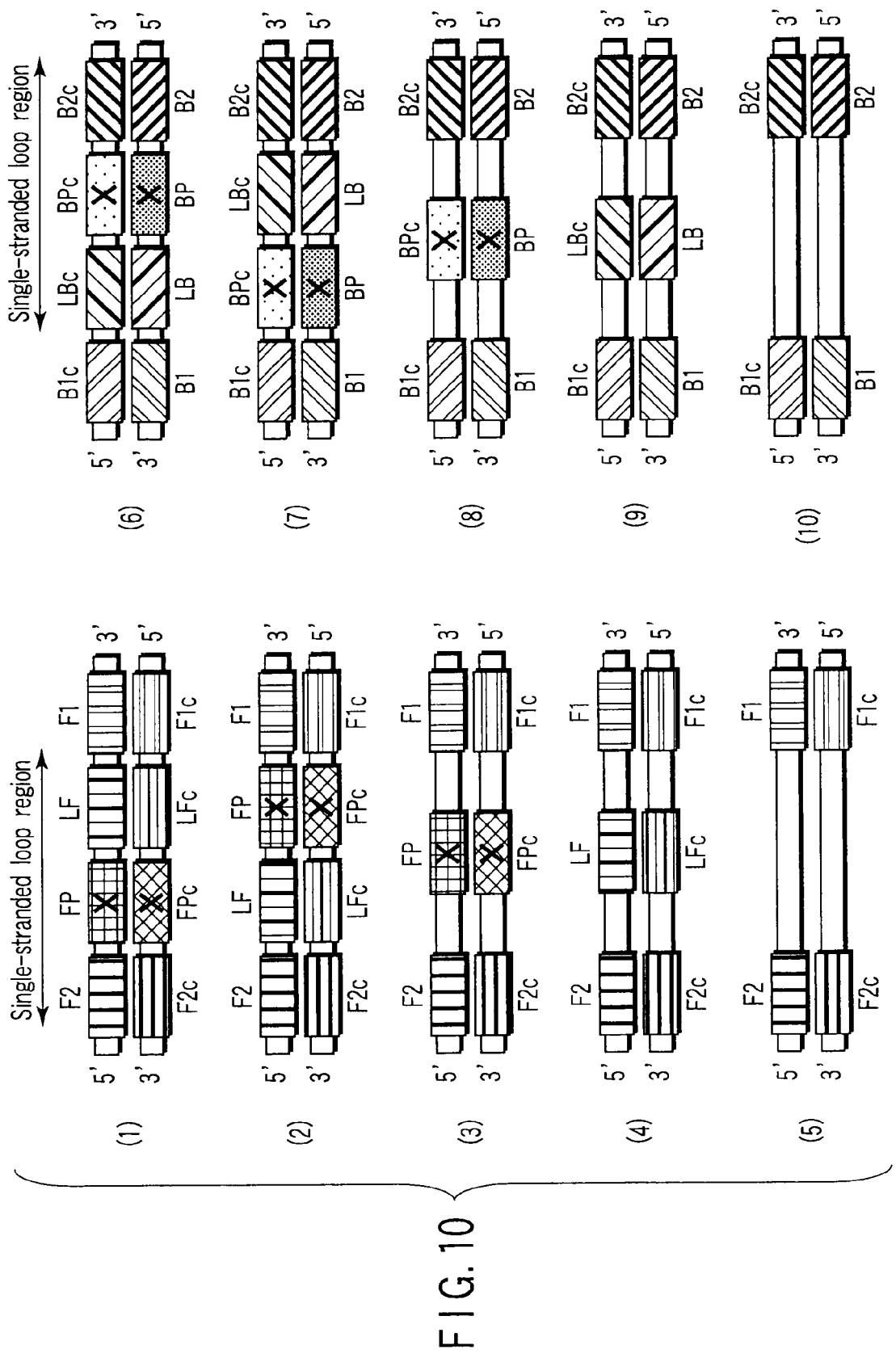
FIG. 10 is a chart showing the design patterns of respective regions in an aspect where single-nucleotide mutation is to be detected.

FIG. 10 shows the design pattern of respective regions in the plus or minus chain of the target nucleic acid, when single-nucleotide mutation is to be detected. In FIGS. 10(1) and 10(2), both a detection sequence and a loop primer region sequence are placed in the F region side. In the case of FIG. 10(1), the F2 or LF region or its complementary chain site is placed at a position not overlapping the single-nucleotide mutation site contained in the FP or FPc region. Thus, the F2 region may overlap the FP region to the base adjacent to the mutation site. Similarly, the LF region may overlap the FPc region to the base adjacent to the mutation site.

The LF and F1 regions preferably have an overlapping region of 20 bases or less, more preferably an overlapping region of 10 bases or less. A greater number of bases overlapped in the LF and F1 regions is undesirable, because it demands annealing of the loop primer LFc on the double-stranded F1-F1c region, leading to deterioration of amplification efficiency.

In FIG. 10(2), the single-nucleotide mutation site contained in the FP region is placed as separated from the LF region. In other words, the LF region may overlap the FP region to the base adjacent to the mutation site. The overlapping region between the FP region and the F1 region is preferably less than 15 bases, more preferably zero bases, in length. The base number is preferably in the above range, because a greater base number of the FP and F1 overlapping region demands hybridization of the probe with the double-stranded F1-F1c region, leading to deterioration of hybridization efficiency.

The base number of the F2 and LF overlapping region is preferably 20 bases or less, more preferably 10 bases or less. A greater base number of the F2 and LF overlapping region leads to expansion of the sequence regions where the F2 sequence in the inner primer and the loop-primer FPc sequence are complementary to each other and to interaction between the primers, and consequently to deterioration of reactivity with the target nucleic acid on which it anneals and in amplification efficiency. Accordingly, the base number is preferably in the range above.

In FIG. 10(3), there is no loop primer placed in the F region side. As with FIGS. 10(1) and 10(2), the F2 region may overlap the FP region to the base adjacent to the mutation site, and the number of bases in the overlapping region between the FP and F1 regions is preferably less than 15, more preferably zero.

In FIG. 10(4), there is no detection sequence placed in the F region side. The case of FIG. 10(4) may be combined with the case shown in FIGS. 10(6) to (8) in which there is a detection sequence in the B region. As with the cases of FIGS. 10(1) and (2), the numbers of the overlapping regions between the F2 and LF regions and the LF and F1 regions are preferably 20 or less, more preferably 10 or less.

In FIG. 10(5), there is no loop primer or detection sequence placed in the F region side. The case of FIG. 10(5) may be combined with the case shown in FIGS. 10(6) to (8) in which there is a detection sequence in the B region. The F2 and F1 regions may be separated by 5 bases or more for improvement in self-annealing efficiency.

FIGS. 10(6) to (10) show the cases of the B region, which are the same as the cases of the F region side. The case shown in FIG. 10(9) or (10) in which there is no detection sequence may be combined with the case shown in FIGS. 10(1) to (3) in which there is a detection sequence in the F region.

In detecting single-nucleotide mutation, if the detection sequence region or the sequence region of its complementary chain, and the loop primer sequence region are placed in the same loop, the single-stranded loop region becomes a long chain lower in self-annealing efficiency, leading to deterioration of amplification efficiency, depending on the sequence of the target nucleic acid. In such a case, it is effective to use a method of shortening the loop region by eliminating the loop primer in the detection sequence-containing loop and place the loop primer in the other loop containing no detection sequence.

In a fifth aspect, the present invention provides a detection method of amplifying a target nucleic acid by the LAMP method and detecting it with a probe nucleic acid, or a method of amplifying a target nucleic acid containing single-nucleotide mutation by the LAMP method and detecting the single-nucleotide mutation with a probe nucleic acid. In the fifth aspect, the target nucleic acid is amplified by the LAMP method by using a primer designed in the first to fourth aspects and the amplification product is detected by hybridization with a probe nucleic acid.

The probe nucleic acid for use has a sequence complementary to the detection sequence (FP, FPc, BP, or BPc), as described above. The probe nucleic acid may be prepared for any one of the detection sequences or for multiple detection sequences. The probe nucleic acid may be present as dissolved in solution, or alternatively, may be immobilized, for example, on an aggregation carrier or a solid-phase support.

The probe nucleic acid may be unlabeled or labeled with a fluorescent material such as Cy5, Cy3, FITC or rhodamine, a light-emitting substance such as luminol, lucigenin or an acridinium ester derivative, hapten or an enzyme, according to the detection method. Yet alternatively, the probe nucleic acid may be modified with a reactive functional group such as amino, carboxyl, hydroxyl, thiol, or sulfone group or with a substance such as avidin or biotin, for immobilization of the probe nucleic acid on the support.

Examples of the supports on which the probe nucleic acid is immobilized include nitrocellulose film, nylon film, microtiter plate, glass, electrode, magnet, beads, plastics, latex, synthetic resins, natural resins, optical fiber, and the like.

Alternatively, a DNA chip may be formed with the probe nucleic acid. The DNA chip is a device having a substrate such as glass or silicon and probe nucleic acids immobilized thereon at high density that allows acquisition of much gene sequence information. The current mainstream fluorescent detection method is a method of detecting a fluorescent-labeled sample gene with a high-sensitivity fluorescence analyzer after allowing it to react with a probe on chip. Also under development as an alternative detection method is an electric current-detecting DNA chip. It is a method of hybridizing a probe nucleic acid immobilized on an electrode with a target nucleic acid, adding an intercalating agent that reacts with double-stranded chain DNAs specifically, and measuring the electrochemical signal obtained from the intercalating agent. The electrochemical DNA chip, which demands no labeling or no expensive device for detection, is attracting attention as a second-generation DNA chip (see, e.g., JP-A 5-199898 [KOKAI]).

When two or more probe nucleic acids are used, unlabeled and labeled probes, or probes immobilized or unimmobilized on solid phase, may be used at the same time, according to the detection method. For example, in the sandwich hybridization using a probe nucleic acid for capturing and a labeled probe nucleic acid for detection, the labeled probe nucleic acid is hybridized with the detection sequence as it is dissolved in a solution, but the probe nucleic acid for capturing may be immobilized on a support after dissolved in solution and hybridized with the detection sequence or may be immobilized previously on the support.

Hybridization and Reaction Condition

Hybridization between the amplification product and the probe nucleic acid is carried out under a suitable condition. The suitable condition varies according to the kind and structure of the amplification product, the kind of the bases contained in the detection sequence, and the kind of the probe nucleic acid. It is carried out, for example, in a buffer solution at an ionic strength in the range of 0.01 to 5 and a pH in the range of 5 to 10. Other additives, for example, a hybridization accelerator such as dextran sulfate, salmon sperm DNA, bovine thymic DNA, EDTA and a surfactant, may be added to reaction solution. The reaction temperature is, for example, in the range of 10° C. to 90° C., and the reaction may be accelerated by agitation or shaking. After reaction, the support may be washed, for example, with a buffer solution at an ionic strength in the range of 0.01 to 5 and a pH in the range of 5 to 10.

Detection Method

Any method may be used for detecting an amplification product hybridized with a probe nucleic acid. Typical examples thereof include the followings:

The first detection method is a method of using an intercalating agent binding to nucleic acid double-stranded chains. In the method, the probe nucleic acid is modified with a reactive functional group such as amino, carboxyl, hydroxyl, thiol, or sulfone group or with a substance such as hapten, avidin, or biotin, and immobilized on a solid phase. The amplification product and the probe nucleic acid immobilized on a solid phase are hybridized with each other, and the resulting support is then washed. Hybridization between the probe nucleic acid and the amplified product is detected with a signal of the intercalating agent bound to the double-stranded chains.

The intercalating agent is not particularly limited, as long as it is photochemically or electrochemically active. Examples thereof include ethidium, ethidium bromide, acridine, aminoacridine, acridine orange, proflavin, ellipticine, actinomycin D, daunomycin, mitomycin C, Hoechst 33342, Hoechst 33258, aclarubicin, DAPI, adriamycin, epirubicin, aclacinomycin, and the like. Other usable intercalating agents include those described in JP-A 62-282599 (KOKAI).

In addition to substances described above reversible in oxidation/reduction reaction, metal complexes containing a substance electrically reversible in oxidation/reductive reaction as the central metal, i.e., metallointercalators, may be used as the intercalating agents in detecting electrochemical change by using an electrode. Examples of the metallointercalators include tris(phenanthroline)zinc complexes, tris(phenanthroline)ruthenium complexes, tris(phenanthroline) cobalt complexes, di(phenanthroline)zinc complexes, di(phenanthroline)ruthenium complexes, di(phenanthroline) cobalt complexes, bipyridine platinum complexes, terpyridine platinum complexes, phenanthroline platinum complexes, tris(bipyridyl)zinc complexes, tris(bipyridyl) ruthenium complexes, tris(bipyridyl)cobalt complexes, di(bipyridyl)zinc complexes, di(bipyridyl)ruthenium complexes, and di(bipyridyl)cobalt complexes.

When performing gene detection by using an electrode, it is possible to use an intercalating agent showing electrochemical light emission. Such an intercalating agent is not particularly limited, and examples thereof include luminol, lucigenin, pyrene, diphenylanthracene, and rubrene. The electrochemical light emission by these intercalating agents can be amplified with an enhancer, for example, a luciferin derivative such as firefly luciferin or dehydroluciferin, phenols such as phenylphenol or chlorophenol, or naphthols.

When an optically active intercalating agent is used, the difference in signal between when the intercalating agent is alone and when it is bound to a double-stranded chain is detected, based on optical information, such as absorbance, fluorescence, light emission, light quenching, fluorescent polarization, or circular dichroism, or on the change in absorption wavelength, fluorescent wavelength, emission wavelength, or quenched light wavelength of the intercalating agent bound to a double-stranded chain. When an electrochemically active intercalating agent is used, the oxidation/ reduction current of the central metal or the intercalating agent itself is measured for detection.

In the second detection method, a method of sandwich-hybridizing a capturing probe nucleic acid with a labeled probe nucleic acid for detection can be used. The probe nucleic acid for capturing is immobilized on a solid phase according to the method described in the first detection method. The substance labeling the nucleic acid to be detected may be determined according to the subsequent detection method used. Examples thereof include electrode active materials, fluorescent materials, light-emitting substances, electrochemical light-emitting substances, enzymes, enzyme substrates, hapten, antigens, antibodies, radio isotopes, and the like. When a substance prohibiting direct signal detection such as hapten is used, the gene is detected indirectly by using an enzyme-bound anti-hapten antibody such as enzyme-bound avidin, by measuring the optical information, such as turbidity, absorbance, fluorescence, light emission, light quenching, fluorescent polarization, or circular dichroism, or the electrical activity of the substance during enzyme reaction.

Alternatively when the DNA chip is made of a probe nucleic acid, the gene may be detected, for example, by a fluorescence-detecting method or a current-detecting method.

When using the current-detecting method with an intercalating agent binding to nucleic acid double-stranded chains, the analyte substance is detected generally according to the first detection method, placing electrodes on a substrate of glass or silicon and immobilizing a probe nucleic acid on the electrodes. The number and placement of the electrodes can be determined easily as needed by those who are skilled in the art. A counter electrode and a reference electrode may also be used additionally, as in other common electrochemical detection methods.

The electrode for use is not particularly limited, and examples of the materials for the electrode include pure metals such as gold, silver, platinum, mercury, nickel, palladium, silicon, germanium, gallium, and tungsten and the alloys thereof; carbons such as graphite and glassy carbon; and the oxides and compounds thereof.

Subsequently, the target nucleic acid is then allowed to hybridize with the probe nucleic acid immobilized on the electrode and then, an electrochemically active intercalating agent is added. Hybridization between the target nucleic acid and the probe nucleic acid on the substrate is detected with the electrochemical signal from the intercalating agent.

The electrochemical measurement is performed, for example, by applying a voltage higher than that causing electrochemical reaction of the intercalating agent and measuring the reaction current derived from the intercalating agent. The voltage may be altered linearly, or may be applied in the pulse shape or at a constant voltage. The current or voltage during measurement may be controlled by using a device such as potentiostat, digital multimeter, or function generator.

Examples of the intercalating agents entering the double-stranded chain include electrochemically active substances such as Hoechst 33258, acridine orange, quinacrine, daunomycin, metallointercalators, bisintercalators such as bisacridine, trisintercalators, polyintercalators, and the like. In addition, the intercalator may be modified with an electrochemically active metal complex such as ferrocene or viologen.

In the case of the fluorescence detection method, used is a method of labeling the probe nucleic acid with a fluorescence colorant such as Cy5, Cy3, FITC, or rhodamine, and sandwich-hybridizing the target nucleic acid according to the second detection method, or a method of labeling the target nucleic acid, for example, with a primer or dNTP labeled with a fluorescence colorant and then hybridizing it with a probe nucleic acid immobilized on a solid phase. The target nucleic acid bound to the probe nucleic acid on the solid phase is detected with a suitable detecting device properly selected according to the kind of the label used.

Analyte Sample

The sample to be analyzed in the present invention is not particularly limited, and examples thereof include blood, serum, leukocyte, urine, feces, semen, saliva, tissue, biopsy sample, oral mucosa, cultured cell, sputum, and the like collected from individuals. The individual may be human, animal other than human, plant, or microbial organism such as virus, microbe, bacteria, yeast or mycoplasma. Nucleic acid components are extracted from these analyte samples, for preparation of a sample solution used in the target nucleic acid detection test. The extraction method is not particularly limited, and examples thereof include commercially available nucleic acid extraction kits such as QIAamp (manufactured by QIAGEN) and Sumaitest (manufactured by Sumitomo Metal Industries, Ltd.), and the like.

Primer

Nucleic acid synthesis from the inner primer should be initiated before synthesis from the outer primer in the LAMP reaction, and thus, the melting temperature (Tm) of the inner primer should be higher than that of the outer primer and/or the amount of the inner primer greater than that of the outer primer for efficient reaction. More specifically, the melting temperature (Tm) preferably satisfies the following formula: (melting temperature of F3-F3c or B3-B3c regions)≦(melting temperature of F2-F2c or B2-B2c regions)≦(melting temperature of F1-F1c or B1-B1c regions). The formula (melting temperature of F2-F2c or B2-B2c regions) (melting temperature of F1-F1c or B1-B1c regions) is ensured to make intramolecular annealing between F1 and F1c and between B1 and B1c proceed preferentially before annealing of F2 or B2 on the loop region. As for the ratio of the primers, the concentration of the inner primer is 2 to 50 times, preferably 4 to 25 times, larger than that of the outer primer.

Primer Length

The chain length of the six kinds of primers used in the LAMP reaction is preferably 10 to 100 bases. The inner primer has two regions bound to each other, and the chain length of the inner primer is that of each region. The length of 10 bases or more is a length needed for annealing of the primer on a template, while specificity is preserved. As it is difficult to prepare an excessively lengthy base by chemical synthesis, the chain length is preferably in the range above.

The distance from the F2c region to the F1c region and from the B2c region to the B1c region which is the single-stranded loop region, i.e., the base number, is preferably zero to 120 bases, more preferably 5 to 70 bases. The regions F2c and B2c are not included in the value. The chain length above is desirable, because an excessively longer or shorter single-stranded loop region results in inefficient self-annealing.

The base number of the chain between the F1 and B1 regions (excluding F1 and B1 regions) may be zero, but is preferably 10 or more. A shorter-length chain between the regions F1 and B1 may lead to unstabilized amplification. The base number of the chain between the regions F2 and B2 (including F2 and B2 regions) is preferably 700 or less, more preferably 500 or less, although it depends on the activity of the strand-displacing polymerase used.

DNA Polymerase

Examples of the strand-displacing DNA polymerases include Bst DNA polymerase, Bca(exo-)DNA polymerase, Vent DNA polymerase, Vent(exo-)DNA polymerase, Deep-Vent DNA polymerase, DeepVent(exo-)DNA polymerase, and the like, as well as the DNA polymerases described in Japanese Patent No. 3313358.

LAMP Reaction Condition

The temperature and pH of the LAMP reaction are adjusted dependent on the DNA polymerase enzyme to give it a favorable activity. In addition, a salt may be appropriately added for adjustment of the enzyme activity or the melting temperature (Tm) of the nucleic acid. Examples thereof include KCl, NaCl, $(NH_4)_2SO_4$, and the like. In addition, adjustment agent of melting temperature (Tm) such as betaine, DMSO, or the like may be used. Also, enzyme protectant such as bovine serum albumin or saccharide, or the like may be used. See JP 3313358 for details.

EXAMPLES

Hereinafter, the present invention will be described specifically with reference to Examples.

Example 1

Detection of Pseudopositive Signal Caused by Inner Primer

Detection Sequence

Figure 11:
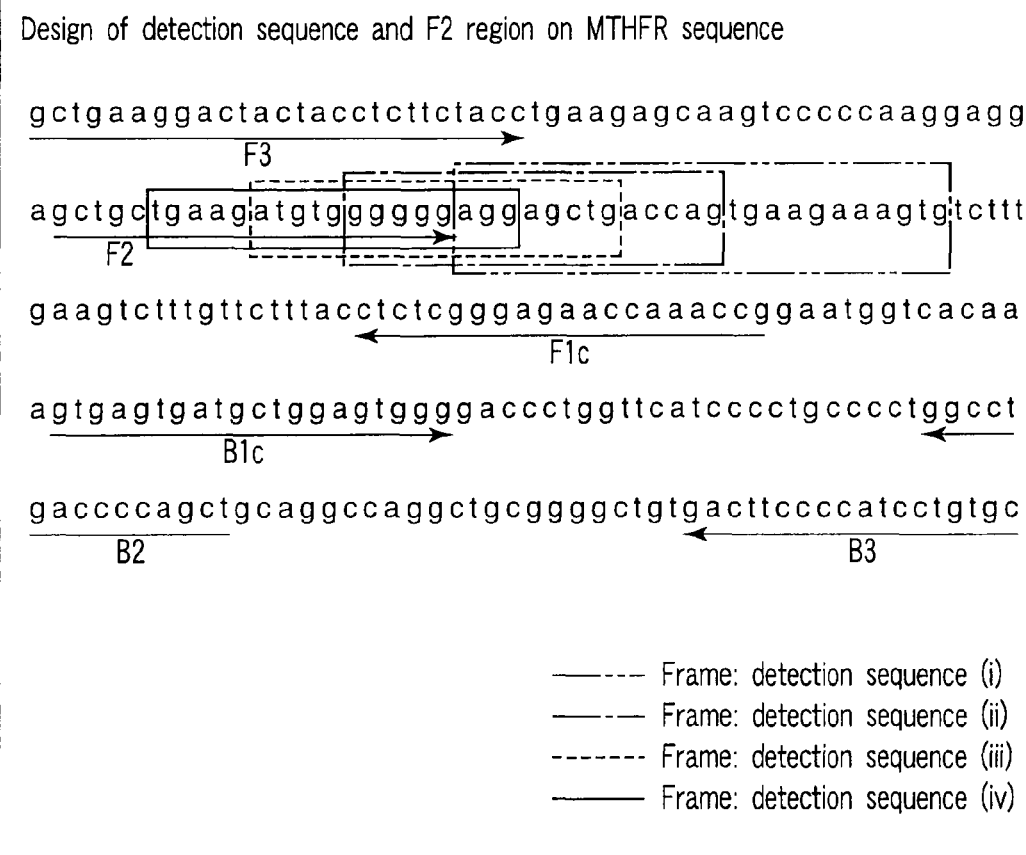
FIG. 11 is a chart showing an embodiment of detection sequences designed on MTHFR gene (SEQ ID NO: 56)

In the present Example, human MTHFR gene was used as the sample nucleic acid. The detection sequence was placed in the single-stranded loop region of the MTHFR LAMP product, either with (i) 0, (ii) 5, (iii) 10, or (iv) 15 bases overlapping the F2 sequence of FIP primer (FIG. 11).

```
(i)    AGGAGCTGACCAGTGAAGAAAGTG   (SEQ ID NO: 1)

(ii)   GGGGGAGGAGCTGACCAG         (SEQ ID NO: 2)

(iii)  ATGTGGGGGAGGAGCTG          (SEQ ID NO: 3)

(iv)   TGAAGATGTGGGGGAGG          (SEQ ID NO: 4)
```

Primer

The synthetic nucleotide primers used in the present Example are listed below. FIG. 11 shows the sequence region of each primer in the human MTHFR gene. The FIP primer contains F1c and F2 regions, and the BIP primer contains B1c and B2 regions. Any sequence may or may not be inserted between them. In FIG. 11, a reverse chain having a sequence complementary to the sequence shown in FIG. 11 was used as the c-added region (i.e., F1c) in the F region, while a reverse chain having the sequence shown in FIG. 11 as the non-c-added regions (i.e., B2 and B3) in the B region.

```
MTHFR F3 primer
GCTGAAGGACTACTACCTCTTCTACC  (SEQ ID NO: 5)

MTHFR FIP primer
CGGTTTGGTTCTCCCGAGAG(F1c)   (SEQ ID NO: 6)

-GCTGCTGAAGATGTGGGGGG(F2)   (SEQ ID NO: 7)

MTHFR B3 primer
GCACAGGATGGGGAAGTC          (SEQ ID NO: 8)

MTHFR BIP primer
GTGAGTGATGCTGGAGTGGG(B1c)-  (SEQ ID NO: 9)

AGCTGGGGTCAGGCC(B2)         (SEQ ID NO: 10)
```

LAMP Reaction Solution

A solution for LAMP reaction was prepared according to the following. The LAMP reaction performed with a human or mouse genome as the template. A LAMP reaction solution was allowed to hybridize with a probe nucleic acid immobilized on a gold electrode. Then, the detection sequence present in the LAMP amplification product was detected by using a current-detecting method.

The LAMP reaction solution comprising:
Sterilized ultrapure water 5.5 µL
Bst DNA polymerase 1 µL
Buffer 12.5 µL
Tris.HCl pH 8.0 40 mM
KCl 20 mM
$MgSO_4$ 16 mM
$(NH_4)_2SO_4$ 20 mM
Tween 20 0.2%
Betaine 1.6 M
DNTP 2.8 mM
F3-primer (10 µM) 0.5 µL
B3-primer (10 µM) 0.5 µL
FIP-primer (20 µM) 2 µL
BIP-primer (20 µM) 2 µL
30 ng/µl template (purified human or mouse genome) 1 µL
Total amount 25 µL Amplification Reaction by LAMP Method A sample was amplified by using human or mouse genomes, or by using sterile ultrapure water replacing the template as control, in the LAMP reaction solution having the composition above at 63° C. for 120 minutes. Agarose electrophoresis of the amplification product showed bands associated with amplification in the product amplified with the human genome template, but no amplification band in the product amplified with the mouse genome and sterile ultrapure water replacing the template. There was white precipitate observed in the solution of the product amplified with the human genome template after amplification, but there was no while precipitate in the solutions of the product amplified with the mouse genome template and the product amplified with the sterile ultrapure water. The white precipitation is a phenomenon observed in the solution caused by a byproduct formed in the amplification process, magnesium pyrophosphate, during LAMP amplification.

These results indicated that the product amplified with the human genome template was formed in specific amplification reaction, while no amplification reaction occurred when the sample was amplified with the mouse genome template or sterile ultrapure water replacing the template.

Preparation of Probe Nucleic Acid-Immobilized Electrode

The nucleotide sequences of the probe nucleic acids used are shown below.

```
Negative probe
GACTATAAACATGCTTTCCGTGGCA       (SEQ ID NO: 11)

Positive probe
(i) CACTTTCTTCACTGGTCAGCTCCT     (SEQ ID NO: 12)

Positive probe
(ii) CTGGTCAGCTCCTCCCCC          (SEQ ID NO: 13)

Positive probe
(iii) CAGCTCCTCCCCCCACAT         (SEQ ID NO: 14)

Positive probe
(iv) CCTCCCCCCACATCTTCA          (SEQ ID NO: 15)
```

The positive probes (i) (ii) (iii) and (iv) were minus chain modified 5'-terminal with SH-group. The negative probe had a sequence unrelated to the MFHFR gene sequence and modified 5'-terminal with SH-group.

Each probe was immobilized on a gold electrode, with the strong chemical bonding potential between a thiol group and gold. A solution containing probe was spotted on the gold electrode and left at 25° C. for 1 hour, and then, the electrode was immersed in 1-mM mercaptohexanol solution and washed with 0.2×SSC solution. The same probe solution was spotted on three electrodes. After washing, the electrode was washed with ultrapure water, and dried in air, to give a probe-immobilized electrode substrate.

Electrode Allocation

Electrodes 1 to 3 : negative probe

Electrodes 4 to 6 : positive probe (i)

Electrodes 7 to 9 : positive probe (ii)

Electrodes 10 to 12 : positive probe (iii)

Electrodes 13 to 15 : positive probe (iv)

Preparation of Reaction Solution and Hybridization

The reaction solution comprised the product amplified with the human or mouse genome or sterile ultrapure water as template respectively, and added a salt diluted to a final concentration of 2×SSC. Separately, a solution at a final concentration of 2×SSC was also prepared as the control. Each of these solutions was spotted on the probe nucleic acid-immobilized electrode substrate prepared above and left at 35° C. for 60 minutes, allowing progress of hybridization reaction. Then, the electrodes were cleaned with ultrapure water slightly. The electrode was immersed in a phosphate buffer containing 50 μM of an intercalating agent Hoechst 33258 for 15 minutes, and the oxidation current response of the Hoechst 33258 molecule was measured.

Results

As shown in FIG. 12, the control 2×SSC solution indicated no increase in signal intensity on the positive probe (i) to (iv)-immobilized electrodes, compared to the current observed on the negative probe (NP)-immobilized electrode. On the other hand, with the product amplified with the human genome template, observed were signals associated with hybridization on all the positive probe (i) to (iv)-immobilized electrodes.

Although there was no amplification reaction occurring with the product amplified with the mouse genome template and the product amplified with sterile ultrapure water replacing the template, a pseudopositive signal of an oligonucleotide having 15 bases overlapping the F2 region was observed from the positive probe (iv). In addition, the pseudopositive signal disappeared, as the number of overlapping bases in the positive probe was reduced, i.e., when the positive probe was changed from positive probe having ten overlapping bases (iii) and positive probe having five overlapping bases (ii) to positive probe having no overlapping base (i).

These results indicated that overlapping of the detection sequence and the inner primer sequence in the single-stranded loop gave rise to a pseudopositive signal. Seemingly, it is because the probe nucleic acid having a sequence complementary to the detection sequence hybridizes with the inner primer. Obviously, presence of an overlapping region of 15 bases results in a distinct pseudopositive signal, prohibiting accurate detection results.

Example 2

Detection of Pseudopositive Signal Caused by Loop Primer

Detection Sequence

Figure 13:
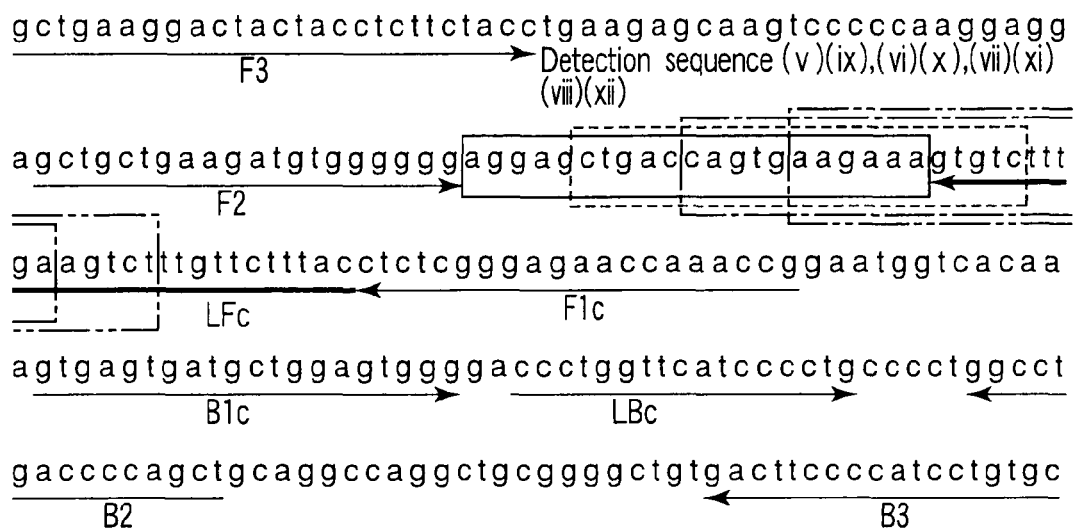
FIG. 13 is a chart showing examples of detection sequences designed on MTHFR gene (SEQ ID NO: 56.

In the present Example, human MTHFR gene was used as sample nucleic acid, as in Example 1. The detection sequence was placed in the single-stranded loop region of the MTHFR LAMP product. The detection sequences used were four kinds of detection sequences respectively having (v) no bases, (vi) 5 bases, (vii) 10 bases, and (viii) 15 bases overlapping the sequence of the loop primer LFc (FIG. 13).

```
(v)      TTTCTTCACTGGTCAGCTCCT  (SEQ ID NO: 16)
(vi)     GACACTTTCTTCACTGGTCAG  (SEQ ID NO: 17)
(vii)    TCAAAGACACTTTCTTCACTG  (SEQ ID NO: 18)
(viii)   AGACTTCAAAGACACTTTCTT  (SEQ ID NO: 19)
```

1) Primer

The synthetic nucleotide primers used in the present Example are shown below. FIG. 13 shows the sequence region of each primer in human MTHFR gene. The FIP primer has F1c and F2 regions, while the BIP primer has B1c and B2 regions. The sequence regions were expressed similarly to Example 1.

```
MTHFR F3 primer
GCTGAAGGACTACTACCTCTTCTACC       (SEQ ID NO: 20)

MTHFR FIP primer
CGGTTTGGTTCTCCCGAGAG(F1c)        (SEQ ID NO: 21)

-GCTGCTGAAGATGTGGGGGG(F2)        (SEQ ID NO: 22)

MTHFR B3 primer
GCACAGGATGGGGAAGTC               (SEQ ID NO: 23)

MTHFR BIP primer
GTGAGTGATGCTGGAGTGGG(B1c)        (SEQ ID NO: 24)

-AGCTGGGGTCAGGCC(B2)             (SEQ ID NO: 25)

MTHFR LFc primer
GTAAAGAACAAAGACTTCAAAGACAC       (SEQ ID NO: 26)

MTHFR LBc primer
CCCTGGTTCATCCCCTG                (SEQ ID NO: 27)
```

2) LAMP Reaction Solution

A solution for LAMP reaction was prepared according to the following. The LAMP reaction performed with a human or mouse genome as the template. A LAMP reaction solution was allowed to hybridize with a probe nucleic acid immobilized on a gold electrode. Then, the detection sequence present in the LAMP amplification product was detected by using a current-detecting method.

The LAMP reaction solution comprising:
Sterile ultrapure water 1.5 μL
Bst DNA polymerase 1 μL
Buffer 12.5 μL
Tris.HCl pH 8.0 40 mM
KCl 20 mM
$MgSO_4$ 16 mM
$(NH_4)_2SO_4$ 20 mM
Tween 20 0.2%
Betaine 1.6 M
DNTP 2.8 mM F3-primer (10 μm) 0.5 μL
B3-primer (10 μm) 0.5 μL
FIP-primer (20 μm) 2 μL
BIP-primer (20 μm) 2 μL
LFc primer (10 μm) 2 μL
LBC primer (10 μm) 2 μL
30 ng/μl template (purified human or mouse genome) 1 μL
Total amount 25 μL Amplification Reaction by LAMP Method A sample was amplified by using human or mouse genomes, or by using sterile ultrapure water replacing the template as control. In FIG. 14A, four kinds of basic primers (F3, B3, FIP, and BIP primers) and two kinds of loop primers (LFc and LBc primers) were used in the composition described in 2) above. In FIG. 14B, five kinds of primers out of the six kinds of primers above (excluding LFc primer) were added in the composition above, and sterilized water was added instead of the LFc primer. In FIG. 14C, four kinds of primers out of the six kinds of primers (excluding the LFc and LBc primers) were used in the composition described above, and sterilized water was added instead of the LFc and LBc primers.

The LAMP reaction was carried out at 63° C. for 30, 60, 90, or 120 minutes. Agarose electrophoresis of the amplified product similar to Example 1 revealed that the product amplified with the human genome template gave amplification bands with all three kinds of primer sets, while the products amplified with the mouse genome template and with sterile ultrapure water replacing the template gave no amplification band with any of the three kinds of primer sets. There was white precipitate in the solution of the product amplified with the human genome template after amplification, while there was no white precipitate in the solutions of the product amplified with the mouse genome template and with sterile ultrapure water replacing the template. These results confirmed that a specific amplification reaction occurred with the product amplified with the human genome template while no amplification reaction proceeded with the product amplified with the mouse genome template or with sterile ultrapure water replacing the template.

Preparation of Probe Nucleic Acid-Immobilized Electrode

The nucleotide sequences of the probe nucleic acids used are shown below.

```
negative probe
GACTATAAACATGCTTTCCGTGGCA       (SEQ ID NO: 28)

positive probe
(v) AGGAGCTGACCAGTGAAGAAA       (SEQ ID NO: 29)

positive probe
(vi) CTGACCAGTGAAGAAAGTGTC      (SEQ ID NO: 30)

positive probe
(vii) CAGTGAAGAAAGTGTCTTTGA     (SEQ ID NO: 31)

positive probe
(viii) AAGAAAGTGTCTTTGAAGTCT    (SEQ ID NO: 32)
```

The positive probes (v) to (viii) were plus chain modified 5'-terminal with SH-group. The negative probe had a sequence unrelated to the MTHFR gene sequence and modified 5'-terminal with SH-group. Each of the probes was immobilized on a gold electrode, according to a method similar to that in Example 1.

Electrode Allocation
Electrodes 1 to 3 : negative probe
Electrodes 4 to 6 : positive probe (v)
Electrodes 7 to 9 : positive probe (vi)
Electrodes 10 to 12 : positive probe (vii)
Electrodes 13 to 15 : positive probe (viii)

Preparation of Reaction Solution and Hybridization

Three kinds of reaction solutions respectively containing a human genome, a mouse genome, and sterile ultrapure water replacing the genome were subjected to amplification by using three kinds of primer sets A, B and C described above as templates at 63° C. for 120 minutes. After amplification, a salt was added to each reaction solution to a final concentration of 2×SSC. A solution of 2×SSC was also prepared as the control. Each of these solutions was spotted on the probe nucleic acid-immobilized electrode substrate prepared above and left at 35° C. for 60 minutes, allowing hybridization reaction. Then, electrochemical measurement was performed according to a method similar to that in Example 1.

Results

As shown in FIG. 14, with the control 2×SSC solution, no increase in signal was observed from the positive probe (v), (vi), (vii), or (viii)-immobilized electrode, compared to the current from the negative probe-immobilized electrode. On the other hand, increase in the signal from the positive probes (v) (vi) (vii) and (viii) associated with hybridization was observed from the product amplified with the human genome template.

With the product amplified with the mouse genome template and with sterile ultrapure water replacing the template, a pseudopositive signal was detected from a positive probe (viii) having a detection sequence having 15 bases overlapping the sequence of loop primer LFc, although no amplification reaction occurred. The pseudopositive signal decreased, as the number of overlapping bases in the positive probes is reduced, i.e., when the positive probe is changed from positive probe having ten overlapping bases (vii) and positive probe having five overlapping bases (vi) to positive probe having no overlapping base (v).

These result revealed that overlapping of the detection sequence and the loop primer sequence in the single-stranded loop leads to hybridization of the probe nucleic acid having a sequence complementary to the detection sequence with the loop primer in solution, giving a pseudopositive signal.

As shown in FIG. 15, in the present Example, a pseudopositive signal was detected as described above in the case A where the analyte sample was amplified with six kinds of primers including a loop primer LFc placed in the F region side having a region overlapping the detection sequence. Alternatively in the case C where the analyte sample was amplified with four kinds of primers without addition of either loop primer LFc or LBc, the amplification efficiency was lower and it took almost 120 minutes for complete amplification.

Yet alternatively in the case of B where the analyte sample was amplified with five kinds of primers together with a primer having a loop primer LBc only in the B region where there is no detection sequence, the pseudopositive was not detected and the amplification was completed in 60 minutes. These results indicated that, if it was not possible to place a detection sequence or a sequence complementary to the detection sequence and a loop primer in the same loop, a method of placing the loop primer in a loop different from the loop containing the detection sequence or the sequence complementary to the detection sequence was effective in terms of LAMP amplification efficiency and detection efficiency of the amplification product.

Example 3

Inhibition of Hybridization Reaction Between Probe Nucleic Acid and Detection Sequence by Loop Primer Detection Sequence In the present Example, human MTHFR gene was used as the sample nucleic acid as in Example 2. The detection sequence was placed in the single-stranded loop region of the MTHFR LAMP product, and four kinds of detection sequences, sequences complementary to the detection sequence having (ix) no bases, (x) 5 bases, (xi) 10 bases, (xii) 15 bases overlapping the sequence of the loop primer LFc, were prepared (FIG. 13). The detection sequences used in Example 3 are reverse chains of those used in Example 2 (i.e., complementary sequences in the opposite direction).

```
(ix)    AGGAGCTGACCAGTGAAGAAA    (SEQ ID NO: 33)

(x)     CTGACCAGTGAAGAAAGTGTC    (SEQ ID NO: 34)

(xi)    CAGTGAAGAAAGTGTCTTTGA    (SEQ ID NO: 35)

(xii)   AAGAAAGTGTCTTTGAAGTCT    (SEQ ID NO: 36)
```

1) Primer

Primers similar to those used in Example 2 were used.

2) LAMP Reaction Solution

A LAMP reaction solution containing a human genome as the template was allowed to hybridize with a probe nucleic acid immobilized on a gold electrode. Then, the detection sequence present in the LAMP amplification product was detected by using a current-detecting method. The LAMP reaction solution has a composition similar to that in Example 2.

Amplification Reaction by LAMP Method

A. a LAMP reaction solution containing six kinds of primers, B. a LAMP reaction solution containing five kinds of primers without the LFc primer, and C. a LAMP reaction solution containing four kinds of primers without the LFc or LBc primer, respectively containing a human genome additionally as the template, were prepared. Each of these solutions was allowed to react at 63° C. for 30, 60, 90, or 120 minutes. The amplified product was analyzed by agarose electrophoresis. In addition, the amplified product in a solution added with sterile ultrapure water replacing the genome during preparation of the LAMP reaction solution was also analyzed by electrophoresis at the same time, confirming absence of contamination.

Preparation of Probe Nucleic Acid-Immobilized Electrode

The nucleotide sequences of the probe nucleic acids used are shown below.

```
negative probe
GACTATAAACATGCTTTCCGTGGCA      (SEQ ID NO: 37)

positive probe
(ix) TTTCTTCACTGGTCAGCTCCT      (SEQ ID NO: 38)

positive probe
(x) GACACTTTCTTCACTGGTCAG       (SEQ ID NO: 39)

positive probe
(xi) TCAAAGACACTTTCTTCACTG      (SEQ ID NO: 40)

positive probe
(xii) AGACTTCAAAGACACTTTCTT     (SEQ ID NO: 41)
```

The positive probes were minus chain modified 3'-terminal with SH-group. The negative probe had a sequence unrelated to the MTHFR gene sequence and modified 3'-terminal with SH-group. The probe was immobilized on a gold electrode according to a method similar to that in Example 1. The same probe solution was also spotted on three electrodes similarly.

Electrode Allocation

Electrodes 1 to 3 : negative probe
Electrodes 4 to 6 : positive probe (ix)
Electrodes 7 to 9 : positive probe (x)
Electrodes 10 to 12 : positive probe (xi)
Electrodes 13 to 15 : positive probe (xii)

Dilution and Hybridization of LAMP Amplification Product

The reaction solution containing a human genome as the template was amplified by using the primer sets A or B described above at 63° C. for 30 or 60 minutes. Electrophoresis of the amplification product showed that the primer sets A and B gave an amplification band after amplification for 30 minutes thinner than that after amplification for 60 minutes. The result confirmed that the product did not reach saturated amplification after amplification for 30 minutes.

The amplification products in the cases of A and B after reaction for 60 minutes and the amplification product in the case of A after reaction for 30 minutes were diluted with LAMP buffer in a stepwise manner. Then, they were subjected to electrophoresis, together with the amplification product in the case of B after reaction for 30 minutes; and the solutions were diluted to a similar dilution ratio, to make the concentration of these amplification products similar to each other.

Then, a salt was added respectively to the amplification product of B after reaction for 30 minutes, the amplification products of A and B after reaction for 60 minutes which was previously diluted with LAMP buffer, and the amplification product of A after reaction for 30 minutes, respectively to a final concentration of 2×SSC. A solution at a final concentration of 2×SSC was also prepared as the control. Each of these solutions was spotted on the probe nucleic acid-immobilized electrode substrate prepared above and left at 35° C. for 60 minutes, allowing progress of hybridization reaction. Then, the electrode was cleaned with ultrapure water slightly. The electrode was immersed in a phosphate buffer containing 50 μM of an intercalating agent Hoechst 33258 for 15 minutes, and the oxidation current response of the Hoechst 33258 molecule was measured.

Results

Figure 16:
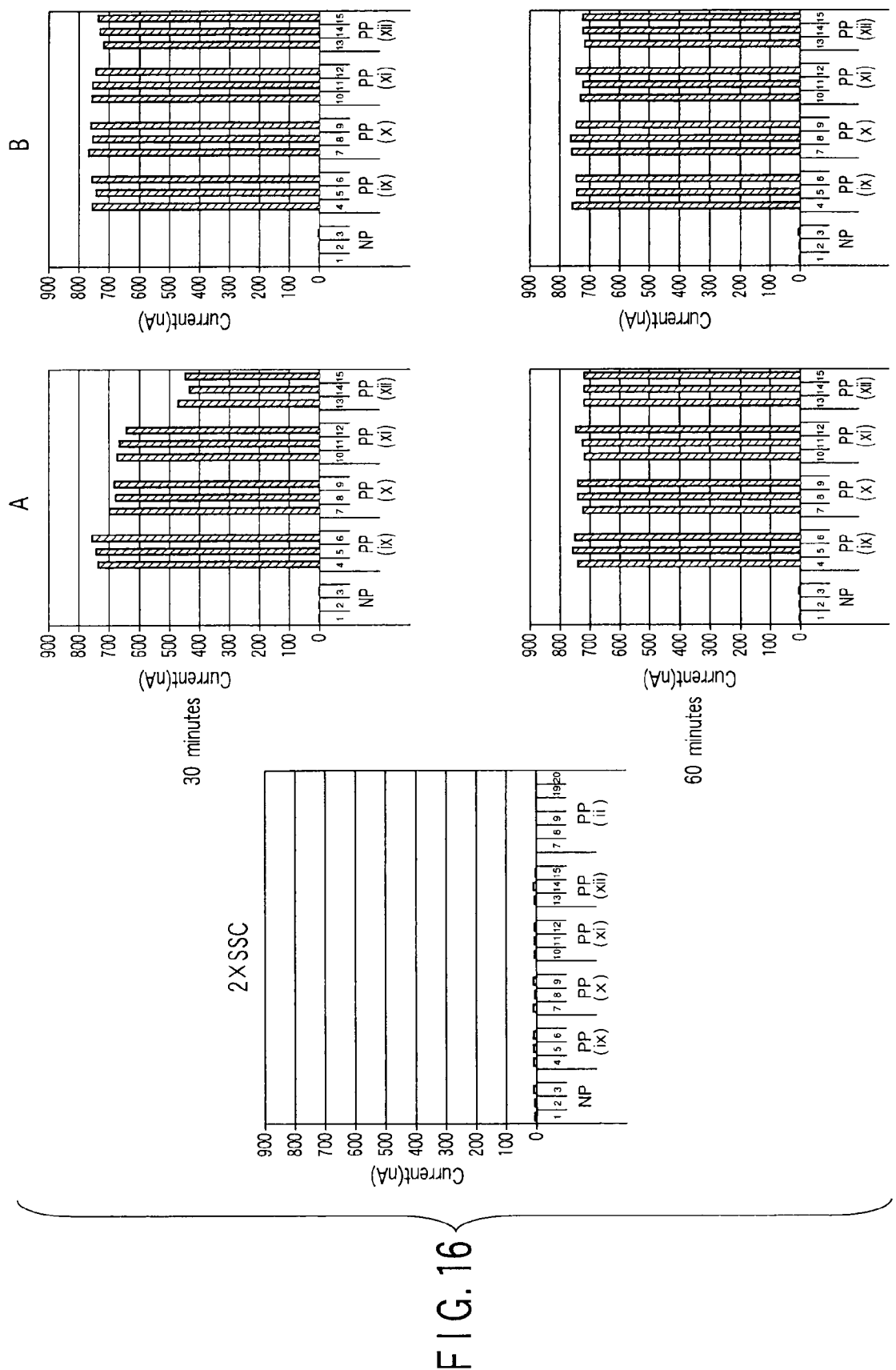
FIG. 16 is a chart showing hybridization inhibition by a loop primer.

As shown in FIG. 16, the amplification products of B after reaction for 60 minutes and 30 minutes showed increase in signal almost at the same level from the electrodes having immobilized positive probes (ix) (x) (xi) and (xii). On the other hand, analysis of the amplification products of A after reaction for 60 minutes and 30 minutes showed that increase in signal from positive probe (xii) having a detection sequence having 15 bases overlapping the sequence of the loop primer LFc was lower after 30 minutes than after 60 minutes. In addition, the increase in signal after reaction for 60 minutes and for 30 minutes became almost the same, as the overlapping region is shortened, i.e., when the positive probe was changed from the positive probe having ten overlapping bases (xi) and the positive probe having five overlapping bases (x) to the positive probe having no overlapping base (ix).

The amplification product of A after reaction for 30 minutes is still under amplification reaction and contains unreacted LFc primer in an amount greater than that of the amplification product of A after reaction for 60 minutes. This indicates that in the solution containing a greater amount of residual unreacted LFc primer, the LFc primer in the solution is annealed preferentially with the single-stranded detection sequence faster than the probe immobilized on a solid phase, leading to deterioration of the hybridization efficiency between the probe and the detection sequence.

Thus shown was that, when the sequence complementary to the detection sequence overlapped the sequence of the primer annealing on the single-stranded loop, the primer remaining in the solution inhibited the hybridization reaction between the probe nucleic acid and the detection sequence, prohibiting accurate measurement result. It is highly probable that such an influence is exerted not only on the loop primer shown in the present Example but also on the inner primer bound to the single-stranded loop.

As shown in FIG. 17, in the case of A where the analyte sample was amplified with six kinds of primers containing the loop primer LFc having a region overlapping the sequence region that was complementary to the detection sequence placed in the F region side in the present Example, inhibition of the hybridization between the probe nucleic acid and the target nucleic acid was observed as shown above. Alternatively, in the case of C where the analyte sample was amplified with four kinds of primers without addition of loop primer LFc or LBc, amplification efficiency is lower, and the period needed for complete amplification was as long as 120 minutes.

Yet alternatively in the case of B where the analyte sample was amplified with five kinds of primers containing a loop primer LBc placed only in the B region where the detection sequence is not placed, there was no hybridization inhibition, and hybridization was completed in 60 minutes. The results indicated that, when a detection sequence or a sequence complementary to the detection sequence and a loop primer cannot be placed in the same loop, a method of placing a loop primer in a loop different from the loop containing the detection sequence or the sequence complementary to the detection sequence is effective in terms of LAMP amplification efficiency and detection efficiency of the amplification product.

Example 4

LAMP Amplification When a Primer is Placed on Single-Nucleotide Mutation Site

In the present Example, human gene N-acetyl transferase 2 (NAT2) was used as sample nucleic acid, and 857 G/A single-nucleotide mutation present in the NAT2 gene was detected (FIG. 18). 857 G/G homo-, 857 A/A homo- and 857 G/A-hetero genes with known sequencing were used as the human genomes. A detection sequence containing single-nucleotide mutation was placed in the single-stranded loop region of the NAT2 LAMP product, and the LAMP-amplification product under the condition shown below was hybridized with a probe nucleic acid immobilized on a gold electrode. After cleaning, the detection sequence present in the LAMP amplification product was detected by a current-detecting method.

Detection Sequence

```
(xiii) ATAGTAAGGGATCCATCACCAGG     (SEQ ID NO: 42)

(xiv)  AAATAGTAAGGGATTCATCACCAGGT (SEQ ID NO: 43)
```

1) Synthetic Nucleotide Primer

```
NAT2 F3 primer
GTGGGCTTCATCCTCAC                    (SEQ ID NO: 44)

NAT2 FIP primer
AGCACTTCTTCAACCTCTTCCTC(F1c)         (SEQ ID NO: 45)

-TAAAGACAATACAGATCTGGTCG(F2)         (SEQ ID NO: 46)

NAT2 B3 primer
TGATAATTAGTGAGTTGGGTGAT              (SEQ ID NO: 47)

NAT2 BIP primer
GGGGAGAAATCTCGTGCCCAA(B1c)           (SEQ ID NO: 48)

-GGGTTTATTTTGTTCCTTATTC(B2)          (SEQ ID NO: 49)

NAT2 LFc primer
AGTGAGAGTTTTAAACTCGACC               (SEQ ID NO: 50)

NAT2 LBc-G primer
CTGGTGATGGATCCCTTAC                  (SEQ ID NO: 51)

NAT2 LBc-A primer
CCTGGTGATGAATCCCTTAC                 (SEQ ID NO: 52)
```

The chain length of the LB-G and LB-A primers placed at the single-nucleotide mutation site was so adjusted that the Tm values thereof become almost the same.

2) LAMP Reaction Solution

The LAMP reaction solution used had a composition similar to that in Example 2. When two primers, LBc-G and LBc-A, were used together as the LBc primers, the concentration of the LBc-G and LBc-A primers are reduced to half respectively.

Amplification Reaction by LAMP Method

A reaction solution was prepared with four kinds of primers without three kinds of loop primers, by using (D) human genome 857 G/G homo and (E) human genome 857 A/A homo as templates.

Separately, the following reaction solutions (F) to (I) were prepared by using human genome 857 G/A hetero as a template: (F) solution containing seven kinds of primers containing all loop primers; (G) solution containing six kinds of primers excluding LBc-A primer; (H) solution containing five kinds of primers excluding LBc-G and LBc-A primers; and (I) solution containing four kinds of primers excluding three kinds of loop primers (LFc, LBc-G, and LBc-A). Respective reaction solutions were allowed to react at 63° C. for 30, 60, 90, or 120 minutes.

The amplification product was analyzed by agarose electrophoresis. The amplification product in a solution containing sterile ultrapure water replacing the genome added during preparation of the LAMP reaction solution was also analyzed by electrophoresis, confirming there was no contamination.

Preparation of Probe Nucleic Acid-Immobilized Electrode

The nucleotide sequences of the probe nucleic acids used are shown below.

```
negative probe
GACTATAAACATGCTTTCCGTGGCA            (SEQ ID NO: 53)

(xiii)positive G probe
CCTGGTGATGGATCCCTTACTAT              (SEQ ID NO: 54)

(xiv)positive A probe
ACCTGGTGATGAATCCCTTACTATTT           (SEQ ID NO: 55)
```

Figure 19:
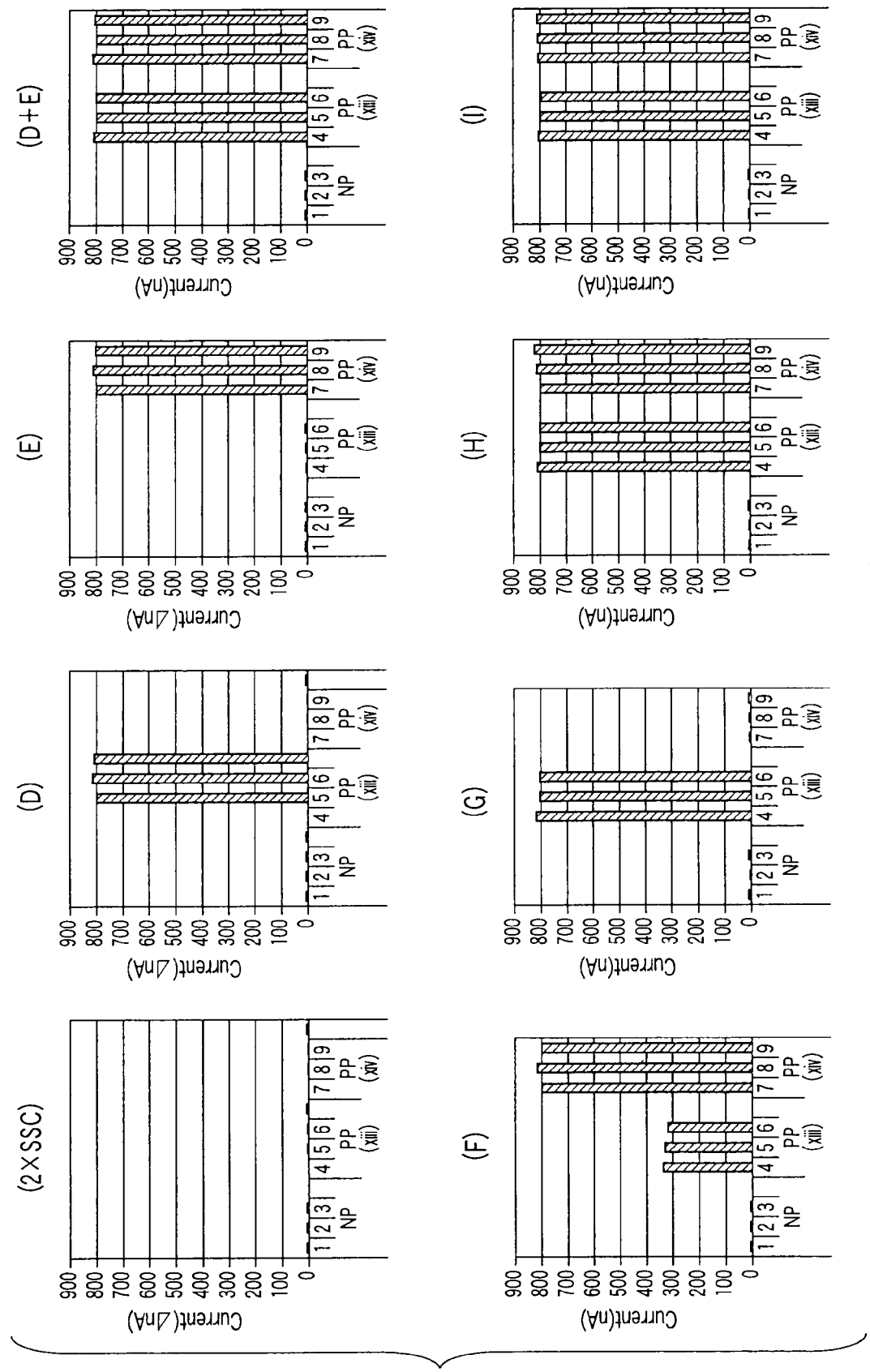
FIG. 19 is a chart showing amplification results when loop primer is placed on the single-nucleotide mutation site.

The positive probes were minus chain modified 3'-terminal with SH-group. The negative probe had a sequence unrelated to the NAT2 gene sequence and modified 3'-terminal with SH-group The probe was immobilized on a gold electrode according to a method similar to that in Example 1. The same probe solution was also spotted on three electrodes similarly.
Electrode Allocation
Electrodes 1 to 3 : negative probe
Electrodes 4 to 6 : positive G probe
Electrodes 7 to 9 : positive A probe
Preparation of Reaction Solution and Hybridization A salt was added to the solution comprising amplification products D, E, F, G, H, and I obtained after reaction at 63t for 60 minutes and also to a mixture D+E of the amplification products D and E in the same amount to a final concentration of 2×SSC. Separately, a solution at a final concentration of 2×SSC was also prepared as the control. Each of these solutions was hybridized with the probe nucleic acid immobilized on a gold electrode at 55° C. for 20 minutes. Then, the electrode was washed with 0.2×SSC buffer at 45° C. for 20 minutes and then slightly with ultrapure water. The electrode was then immersed in a phosphate buffer solution containing 50 μm of an intercalating agent Hoechst 33258 for 15 minutes, and then the oxidation current response from the Hoechst 33258 molecule was measured.
Results As shown in FIG. 19, the LAMP product obtained by using D. human genome 857 G/G homo and E. human genome 857 A/A homo as the templates and no loop primer showed increase in signal from the G or A probe. In addition, the D+E product, artificial hetero product obtained by mixing D and E, showed increase in signal from both the G and A probes almost similar in intensity.

The F product obtained by using 857 G/A hetero human gene as the template and seven kinds of primers including the LBc-A and LBc-G primers made the Tm values of the LBc-A and LBc-G primers similar to each other, but A-typed signal was greater. The results showed that it was difficult to balance the reaction efficiencies of the G- and A-typed primers.

Alternatively, the LAMP reaction solution G containing six kinds of primers including LBc-G primer but excluding LBc-A primer showed a G-typed signal reflecting the genotype of loop primer and almost no A-typed signal. The results indicated that the G amplification product almost did not reflect the genotype of the template, and that the product corresponding to the type of gene introduced into the loop primer was amplified predominantly.

On the other hand, H and I products obtained by using no primer overlapping the mutation site gave a signal accurately reflecting the type of template. These results suggested that it was necessary not to place a primer in the polymorphic (mutational) region, for obtaining an amplification product accurately reflecting the type of the template.

As shown in FIG. 20, as for the relationship between the added primer and the saturation amplification period, the product H having a loop primer LBc annealing on the F region side without overlapping the single-nucleotide mutation site reached saturation of amplification in 30 minutes. On the other hand, amplification for the product I with no added loop primer needed a saturation amplification period of as long as 60 minutes. The results indicated that, when a loop primer cannot be placed in the loop containing a single-nucleotide mutation region or a region of its complementary chain, a method of placing the loop primer in a loop different from the loop containing the single-nucleotide mutation (single-nucleotide mutation) region or the region of its complementary chain is effective in terms of LAMP amplification efficiency and detection efficiency of the amplification product.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An assay kit for use in a method of detecting an amplification product by hybridizing it with a probe nucleic acid, wherein the amplification product is amplified from a target nucleic acid with primers,
    wherein the target nucleic acid comprises F3, F2 and F1 regions in this order from a 5' terminal side; B3c, B2c and B1c regions in this order from a 3' terminal side; an FP region in the region from the F2 to F1 regions and/or a BPc region in the region from the B2c to B1c regions; and further comprises at least one of an LF region in the region from F2 to F1 regions and an LBc region in the region from the B2c to B1c regions;
    wherein the assay kit comprises a FIP primer, a F3 primer, a BIP primer, a B3 primer, at least one of loop primer LFc and LBc, a buffer, a strand-displacing DNA polymerase, a dNTP, and a probe nucleic acid comprising a nucleotide sequence complementary to a sequence selected from the group consisting of sequence in the FP and BPc region and sequences complementary thereto;
    wherein the FIP primer comprises sequence identical to that of the F2 region at the 3' terminal side and sequence complementary to that of the F1 region at the 5' terminal side;
    the F3 primer comprises sequence identical to that of the F3 region;
    the BIP primer comprises sequence complementary to that of the B2c region at the 3' terminal side and sequence identical to that of the B1c region at the 5' terminal side;
    the B3 primer comprises sequence complementary to that of the B3c region; and at least one of a loop primer LFc comprises sequence complementary to that of the LF region and a loop primer LBc comprises sequence identical to that of the LBc region; and
    wherein the primers are designed in such a manner that the FP and F2 regions and/or the BPc and B2c regions have a non-overlapping region of at least 10 bases or more and overlapping regions of 10 bases or less and that the FP and LF regions and/or the BPc and LBc regions have a non-overlapping region of at least 10 bases or more and overlapping regions of 10 bases or less.

2. The kit according to claim 1, wherein the probe nucleic acid is immobilized on a solid-phase support.

3. The kit according to claim 2, wherein the solid-phase support is a DNA chip.

4. An assay kit for use in a method of detecting a single-nucleotide mutation by amplifying a target nucleic acid having a single-nucleotide mutation with primers and hybridizing the amplification product with a probe nucleic acid,
    wherein the target nucleic acid comprises F3, F2 and F1 regions in this order from a 5' terminal side; B3c, B2c and B1c regions in this order from a 3' terminal side; an FP region having the single-nucleotide mutation in the region from the F2 to F1 regions and/or a BPc region having the single-nucleotide mutation in the region from the B2c to B1c regions; and further comprises at least one of an LF region in the region from the F2 to F1 regions and an LBc region in the region from the B2c to B1c regions;
    wherein the assay kit comprises a FIP primer, a F3 primer, a BIP primer, a B3 primer, at least one of a loop primer LFc and LBc, a buffer, a strand-displacing DNA polymerase, a dNTP, and a probe nucleic acid comprising a nucleotide sequence complementary to a sequence selected from the group consisting of sequence in the FP and BPc region, and sequences complementary thereto;

wherein the FIP primer comprises sequence identical to that of the F2 region at the 3' terminal side and sequence complementary to that of the F1 region at the 5' terminal side;

the F3 primer comprises sequence identical to that of the F3 region;

the BIP primer comprises sequence complementary to that of the B2c region at the 3' terminal side and sequence identical to that of the B1c region at the 5' terminal side;

the B3 primer comprises sequence complementary to that of the B3c region; and at least one of a loop primer LFc comprising sequence complementary to that of the LF region and a loop primer LBc comprising sequence identical to that of the LBc region; and wherein the primers are designed such that the F2 region does not overlap the single-nucleotide mutation in the FP region and/or the B2c region does not overlap the single-nucleotide mutation in the BPc region; and the LF region does not overlap the single-nucleotide mutation in the FP region and/or the LBc region does not overlap the single-nucleotide mutation in the BPc region.

5. The kit according to claim 4, wherein the probe nucleic acid is immobilized on a solid-phase support.

6. The kit according to claim 5, wherein the solid-phase support is a DNA chip.

7. A kit comprising:
a FIP primer, wherein the FIP primer comprises sequence identical to that of a F2 region at the 3' terminal side and sequence complementary to that of a F1 region at the 5' terminal side, a F3 primer, comprising sequence identical to that of a F3 region, a BIP primer comprising sequence complementary to that of a B2c region at the 3' terminal side and sequence identical to that of a B1c region at the 5' terminal side;

a B3 primer comprising sequence complementary to that of a B3c region;

at least one of loop primer LFc or LBc, wherein loop primer LFc comprises sequence complementary to that of a LF region, and wherein loop primer LBc comprises sequence identical to that of a LBc region, wherein the primers are designed in such a manner that the FP and F2 regions and/or the BPc and B2c regions have a non-overlapping region of at least 10 bases or more and overlapping regions of 10 bases or less and that the FP and LF regions and/or the BPc and LBc regions have a non-overlapping region of at least 10 bases or more and overlapping regions of 10 bases or less;

wherein said regions are defined in relation to those of a target nucleic acid which comprises F3, F2 and F1 regions in this order from a 5' terminal side; B3c, B2c and B1c regions in this order from a 3' terminal side; an FP region in the region from the F2 to F1 regions and/or a BPc region in the region from the B2c to B1c regions; and further comprises at least one of an LF region in the region from F2 to F1 regions or an LBc region in the region from the B2c to B1c regions.

8. The kit of claim 7, further comprising a probe nucleic acid comprising a nucleotide sequence complementary to a sequence selected from the group consisting of sequence in a FP and BPc region and sequences complementary thereto.

9. The kit of claim 7, further comprising at least one buffer, a strand-displacing DNA polymerase, or dNTP.

10. The kit of claim 7, further comprising at least one polynucleotide comprising the target sequence.

11. The kit of claim 7, further comprising at least one biological sample selected from the group consisting of blood, serum, leukocyte, urine, feces, semen, saliva, tissue, biopsy sample, oral mucosa, cultured cell, and sputum.

12. The kit according to claim 7, wherein the probe nucleic acid is immobilized on a solid-phase support.

13. The kit according to claim 12, wherein the solid-phase support is a DNA chip.

14. The kit of claim 1, further comprising a probe nucleic acid comprising a nucleotide sequence complementary to a sequence selected from the group consisting of sequence in a FP and BPc region and sequences complementary thereto.

15. The kit of claim 1, further comprising at least one buffer, a strand-displacing DNA polymerase, or dNTP.

16. The kit of claim 1, further comprising at least one polynucleotide comprising the target sequence.

17. The kit of claim 1, further comprising at least one biological sample selected from the group consisting of blood, serum, leukocyte, urine, feces, semen, saliva, tissue, biopsy sample, oral mucosa, cultured cell, and sputum.

18. The kit of claim 4, further comprising a probe nucleic acid comprising a nucleotide sequence complementary to a sequence selected from the group consisting of sequence in a FP and BPc region and sequences complementary thereto.

19. The kit of claim 4, further comprising at least one buffer, a strand-displacing DNA polymerase, or dNTP.

20. The kit of claim 4, further comprising at least one polynucleotide comprising the target sequence.

21. The kit of claim 4, further comprising at least one biological sample selected from the group consisting of blood, serum, leukocyte, urine, feces, semen, saliva, tissue, biopsy sample, oral mucosa, cultured cell, and sputum.

* * * * *

SEQUENCE LISTING

```
<160> NUMBER OF SEQ ID NOS: 57

<210> SEQ ID NO 1
<211> LENGTH: 24
<212> TYPE: DNA
<213> ORGANISM: Homo sapiens

<400> SEQUENCE: 1
aggagctgac cagtgaagaa agtg                                           24

<210> SEQ ID NO 2
<211> LENGTH: 18
<212> TYPE: DNA
<213> ORGANISM: Homo sapiens

<400> SEQUENCE: 2
gggggaggag ctgaccag                                                  18

<210> SEQ ID NO 3
<211> LENGTH: 18
<212> TYPE: DNA
<213> ORGANISM: Homo sapiens

<400> SEQUENCE: 3
atgtgggggg aggagctg                                                  18
```

```
<210> SEQ ID NO 4
<211> LENGTH: 18
<212> TYPE: DNA
<213> ORGANISM: Homo sapiens

<400> SEQUENCE: 4
tgaagatgtg gggggagg                                                     18

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gctgaaggac tactacctct tctacc                                            26

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cggtttggtt ctcccgagag                                                   20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gctgctgaag atgtgggggg                                                   20

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcacaggatg gggaagtc                                                     18

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gtgagtgatg ctggagtggg                                                   20

<210> SEQ ID NO 10
<211> LENGTH: 15
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 10
agctggggtc aggcc                                                    15

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
gactataaac atgctttccg tggca                                         25

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
cactttcttc actggtcagc tcct                                          24

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
ctggtcagct cctccccc                                                 18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
cagctcctcc ccccacat                                                 18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15 cctccccca catcttca                                                  18

<210> SEQ ID NO 16
<211> LENGTH: 21
<212> TYPE: DNA
<213> ORGANISM: Homo sapiens
```

```
<400> SEQUENCE: 16
tttcttcact ggtcagctcc t                                           21

<210> SEQ ID NO 17
<211> LENGTH: 21
<212> TYPE: DNA
<213> ORGANISM: Homo sapiens

<400> SEQUENCE: 17
gacactttct tcactggtca g                                           21

<210> SEQ ID NO 18
<211> LENGTH: 21
<212> TYPE: DNA
<213> ORGANISM: Homo sapiens

<400> SEQUENCE: 18
tcaaagacac tttcttcact g                                           21

<210> SEQ ID NO 19
<211> LENGTH: 21
<212> TYPE: DNA
<213> ORGANISM: Homo sapiens

<400> SEQUENCE: 19
agacttcaaa gacactttct t                                           21

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gctgaaggac tactacctct tctacc                                      26

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cggtttggtt ctcccgagag                                             20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gctgctgaag atgtgggggg                                             20

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 23
gcacaggatg gggaagtc                                                18

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gtgagtgatg ctggagtggg                                              20

<210> SEQ ID NO 25
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
agctggggtc aggcc                                                   15

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gtaaagaaca aagacttcaa agacac                                       26

<210> SEQ ID NO 27
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ccctggttca tcccctg                                                 17

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
gactataaac atgctttccg tggca                                        25

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      probe -continued

```
<400> SEQUENCE: 29
aggagctgac cagtgaagaa a                                              21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
ctgaccagtg aagaaagtgt c                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
cagtgaagaa agtgtctttg a                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
aagaaagtgt ctttgaagtc t                                              21

<210> SEQ ID NO 33
<211> LENGTH: 21
<212> TYPE: DNA
<213> ORGANISM: Homo sapiens

<400> SEQUENCE: 33
aggagctgac cagtgaagaa a                                              21

<210> SEQ ID NO 34
<211> LENGTH: 21
<212> TYPE: DNA
<213> ORGANISM: Homo sapiens

<400> SEQUENCE: 34
ctgaccagtg aagaaagtgt c                                              21

<210> SEQ ID NO 35
<211> LENGTH: 21
<212> TYPE: DNA
<213> ORGANISM: Homo sapiens

<400> SEQUENCE: 35
cagtgaagaa agtgtctttg a                                              21

<210> SEQ ID NO 36
<211> LENGTH: 21
<212> TYPE: DNA
<213> ORGANISM: Homo sapiens

<400> SEQUENCE: 36
```
aagaaagtgt ctttgaagtc t                                              21

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37
gactataaac atgctttccg tggca                                          25

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
tttcttcact ggtcagctcc t                                              21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
gacactttct tcactggtca g                                              21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
tcaaagacac tttcttcact g                                              21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
agacttcaaa gacactttct t                                              21

<210> SEQ ID NO 42
<211> LENGTH: 23
<212> TYPE: DNA
<213> ORGANISM: Homo sapiens

<400> SEQUENCE: 42
atagtaaggg atccatcacc agg                                            23

<210> SEQ ID NO 43

```
<211> LENGTH: 26
<212> TYPE: DNA
<213> ORGANISM: Homo sapiens

<400> SEQUENCE: 43
aaatagtaag ggattcatca ccaggt                                          26

<210> SEQ ID NO 44
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gtgggcttca tcctcac                                                    17

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
agcacttctt caacctcttc ctc                                             23

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
taaagacaat acagatctgg tcg                                             23

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tgataattag tgagttgggt gat                                             23

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ggggagaaat ctcgtgccca a                                               21

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 49
gggtttattt tgttccttat tc                                              22

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
agtgagagtt ttaaactcga cc                                              22

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ctggtgatgg atcccttac                                                  19

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cctggtgatg aatcccttac                                                 20

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 53
gactataaac atgctttccg tggca                                           25

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
cctggtgatg gatcccttac tat                                             23

<210> SEQ ID NO 55
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 55
acctggtgat gaatcccta ctattt                                              26

<210> SEQ ID NO 56
<211> LENGTH: 250
<212> TYPE: DNA
<213> ORGANISM: Homo sapiens

<400> SEQUENCE: 56
gctgaaggac tactacctct tctacctgaa gagcaagtcc cccaaggagg agctgctgaa         60
gatgtggggg gaggagctga ccagtgaaga aagtgtcttt gaagtctttg ttctttacct        120
ctcgggagaa ccaaaccgga atggtcacaa agtgagtgat gctggagtgg ggaccctggt        180
tcatcccctg cccctggcct gacccagct gcaggccagg ctgcggggct gtgacttccc         240
catcctgtgc                                                              250

<210> SEQ ID NO 57
<211> LENGTH: 254
<212> TYPE: DNA
<213> ORGANISM: Homo sapiens

<400> SEQUENCE: 57
gtgggcttca tcctcaccta tagaaaattc aattataaag acaatacaga tctggtcgag         60
tttaaaactc tcactgagga agaggttgaa gaagtgctga aaaatatatt taagatttcc        120
ttggggagaa atctcgtgcc caaacctggt gatggaatcc cttactattt agaataagga        180
acaaaataaa cccttgtgta tgtatcaccc aactcactaa ttatcaactt atgtgctatc        240
agatatcctc tcta                                                         254
```